United States Patent
Yamamura et al.

(10) Patent No.: US 8,367,623 B2
(45) Date of Patent: *Feb. 5, 2013

(54) GLYCOLIPID AND MEDICINE FOR AUTOIMMUNE DISEASE CONTAINING THE SAME AS ACTIVE INGREDIENT

(75) Inventors: Takashi Yamamura, Tokyo (JP); Sachiko Miyake, Saitama (JP)

(73) Assignee: Japan as Represented by President of National Center of Neurology and Psychiatry, Tokyo (JP)

( * ) Notice: Subject to any disclaimer, the term of this patent is extended or adjusted under 35 U.S.C. 154(b) by 1817 days.

This patent is subject to a terminal disclaimer.

(21) Appl. No.: 10/486,948

(22) PCT Filed: Aug. 14, 2002

(86) PCT No.: PCT/JP02/08280
§ 371 (c)(1),
(2), (4) Date: Feb. 13, 2004

(87) PCT Pub. No.: WO03/016326
PCT Pub. Date: Feb. 27, 2003

(65) Prior Publication Data
US 2006/0148723 A1    Jul. 6, 2006

(30) Foreign Application Priority Data

Aug. 16, 2001  (JP) ................. 2001-247055

(51) Int. Cl.
*A61K 31/7028*  (2006.01)
*A61P 37/02*  (2006.01)
*C07H 15/04*  (2006.01)
*C07H 15/10*  (2006.01)

(52) U.S. Cl. .......................... 514/25; 536/53
(58) Field of Classification Search .......... 514/25; 523/53
See application file for complete search history.

(56) References Cited

U.S. PATENT DOCUMENTS
(Continued)

FOREIGN PATENT DOCUMENTS

| CN | 1259872 | 7/2000 |
|---|---|---|
| EP | 0 609 437 A1 | 8/1994 |

(Continued)

OTHER PUBLICATIONS

Figueroa-Perez et al. Total synthesis of alpha-galactosyl cerebroside. Carbohydrate Research. 2000;328:95-102.*

(Continued)

(Continued)

Miyamoto et a. A synthetic glycolipid prevents autoimmune encephalomyelitis by inducing Th2 bias of natural killer T cells. Nature. Oct. 4, 2001;413: 531-534.*

*Primary Examiner* — Kortney L Klinkel
(74) *Attorney, Agent, or Firm* — Jenkins, Wilson, Taylor & Hunt, P.A.

(57) ABSTRACT

The invention is a glycolipid useful in treating autoimmune diseases and a medicine thereof as active ingredient for autoimmune diseases, represented by the formula

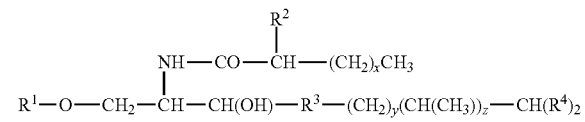

wherein $R^1$ is an aldopyranose group, $R^2$ is a hydrogen atom or a hydroxyl group, $R^3$ is $-CH_2-$, $-CH(OH)-CH_2-$ or $-CH=CH-$, $R^4$ is a hydrogen atom or $CH_3$, x is 0-35, y and z represent integers satisfying y+z=0-3.

14 Claims, 8 Drawing Sheets

U.S. PATENT DOCUMENTS

| | | | |
|---|---|---|---|
| 5,565,433 A * | 10/1996 | Banville et al. | 514/25 |
| 5,627,271 A * | 5/1997 | Flitsch et al. | 536/18.5 |
| 5,767,092 A | 6/1998 | Koezuka et al. | |
| 5,827,828 A | 10/1998 | Buschard et al. | |
| 5,861,520 A * | 1/1999 | Ogawa et al. | 554/42 |
| 5,936,076 A * | 8/1999 | Higa et al. | 536/17.9 |
| 6,376,475 B1 * | 4/2002 | Marth et al. | 514/49 |
| 6,531,453 B1 | 3/2003 | Taniguchi et al. | |
| 6,589,940 B1 * | 7/2003 | Raz et al. | 514/44 |
| 7,273,711 B1 * | 9/2007 | Marth et al. | 435/7.24 |

FOREIGN PATENT DOCUMENTS

| | | |
|---|---|---|
| EP | 0 988 860 A1 | 3/2000 |
| EP | 1 018 548 A1 | 12/2000 |
| WO | WO/92 19633 | 11/1992 |
| WO | 97/26891 A | 7/1997 |

OTHER PUBLICATIONS

Cellular Immunology, vol. 199, pp. 37-42 (2000).
Science, vol. 278, pp. 1626-1629 (1997).
Proceedings of the National Academy of Sciences of the USA, vol. 95, pp. 5690-5693 (1998).
Journal of Medicinal Chemistry, vol. 38, pp. 2176-2187 (1995).
Journal of Immunology, vol. 166, pp. 662-669, (2001).
Iijima H; Kimura K; Sakai T; Uchimura A; Shimizu T; Ueno H; Natori T; Koezuka Y; "Structure-activity relationship and conformational analysis of monoglycosylceramides on the syngeneic mixed leukocyte reaction" Bioorganic and Medicinal Chemistry, vol. 6, No. 10, 1998, pp. 1905-1910.
Buschard K; Hanspers K; Fredman P; Reich E-P; "Treatment with sulfatide or its precursor, galactosylceramide, prevents diabetes in NOD mice" Autoimmunity, vol. 34, No. 1, Jan. 2001, pp. 9-17.

* cited by examiner

GLYCOLIPID AND MEDICINE FOR AUTOIMMUNE DISEASE CONTAINING THE SAME AS ACTIVE INGREDIENT

TECHNICAL FIELD

The present invention relates to a novel glycolipid and a medicine for autoimmune diseases containing it as active ingredient.

BACKGROUND OF THE PRIOR ART

Living bodies have a function to prevent and inhibit the occurrence of autoimmune diseases, and this function is referred to as the "immune modulatory function". NKT cells recently attracted attention as a lymphocyte having the "immune modulatory function". (Saishin Igaku Vol. 55, No. 4, pp. 858-863.) The inventors have been working on the development of medicines that act upon NKT cells (a pharmaceutical drug material that appropriately stimulates NKT cells and effectively expresses their immune modulatory function).

The conventional treatment methods for autoimmune diseases focused mainly on "non-specific immunosuppressive therapy" involving glucocorticoids and immunosuppressants. "Non-specific immunosuppressive therapy" refers to methods of treatment that suppress many of the biological functions of immune cells without special selectivity and distinction. These methods of treatment, therefore, suppress biological reactions inducing and aggravating diseases but they also suppress biological reactions necessary to living bodies (side effects). Therefore, the development of specific immunosuppressants (pharmaceutical drug agents that suppress only the biological reactions that induce and aggravate diseases) is urgently desired. Auto-antigen peptide treatments were recently tested with this goal in mind. However, since peptides are manifested by the major histocompatibility gene complex (MHC) molecules that have individual differences, the difference in efficacy varied tremendously among individuals, and allergic reactions also posed a problem.

Alpha-galactosylceramide has been identified so far as a substance capable of stimulating NKT cells by other researchers. [Science, Vol. 278, pp. 1626-1629 (1997), Proc. Natl. Acad. Sci. USA Vol. 95, pp. 5690-5693 (1998), J. Med. Chem. 1995, 38, pp. 2176-2187, Japanese Patent Application Public Disclosure (Kokai) Hei 5-9193, Japanese Patent Application Public Disclosure (Kokai) Hei 5-59081, Japanese Patent No. 3088461 and U.S. Pat. No. 5,936,076.] The inventors administered the alpha-galactosylceramide described in the publications to treat autoimmune diseases such as the animal model for multiple sclerosis, experimental autoimmune encephalomyelitis (EAE), and collagen induced arthritis, the animal model of rheumatoid arthritis. However, this alpha-galactosylceramide induces both IL-4, a cytokine that suppresses autoimmune diseases, as well as IFN-γ, a cytokine that aggravates autoimmune diseases. Therefore, this alpha-galactosylceramide was found to be clearly not effective in suppressing or treating autoimmune diseases. (American Immunology Society Journal, the Journal of Immunology, Jan. 1, 2001, Vol. 166, pp. 662-669.) That is, conventional alpha-galactosylceramide is not an appropriate medicine for autoimmune disease since it induces a simultaneous manifestation of conflicting functions (a function to suppress disease and a function to aggravate the disease) of NKT cells.

Problems Encountered

The objective of the present invention is to provide glycolipids useful in treating autoimmune diseases. Although alpha-galactosylceramide, previously under study for such a purpose, is recognized definitely to have a capacity to stimulate NKT cells, its effect is non-specific and it also aggravates autoimmune diseases. Thus it was extremely unsatisfactory as such a medicine. The glycolipids of the present invention, however, induce specific cytokines that suppress autoimmune diseases and do not induce other factors that aggravate autoimmune diseases. Therefore, they are extremely effective in treating autoimmune diseases.

SUMMARY OF THE INVENTION

The inventors synthesized a number of glycolipids that are the derivatives of conventional alpha-galactosylceramide and tested their biological activities. As a result, the inventors discovered that the substances, obtained by modifying these glycolipids to shorten the length of the carbon chain in the sphingosine base, displayed the capability to induce only the function (produces IL-4) useful in suppressing autoimmune disease, which is the same one that NKT cells possesses. The derivative was administered to treat EAE, the animal model for multiple sclerosis, and was confirmed to have preventive and treatment effects on EAE.

That is, the present invention is to provide an glycolipid represented by the formula (I) shown below.

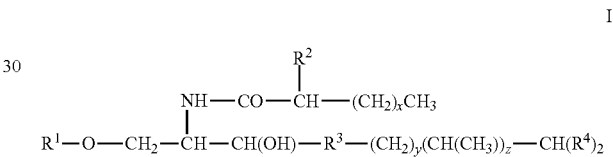

In the formula $R^1$ is an aldopyranose group. As this aldopyranose radical, α-D-glycosyl, α-D-galactosyl, α-D-mannosyl, β-D-glucosyl, β-D-galactosyl, β-D-mannosyl, 2-deoxy-2-amino-α-D-galactosyl, 2-deoxy-2-amino-β-D-galactosyl, 2-deoxy-2-acetylamino-α-D-galactosyl, 2-deoxy-2-acetylamino-β-D-galactosyl, β-D-allopyranosyl, β-D-altropyranosyl, β-D-idosyl and the like can be mentioned, and α-isomer is more effective as the glycolipid of the present invention. Of these, α-D-galactopyranosyl represented by the formula below is preferred as $R^1$.

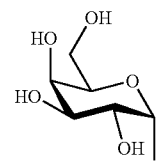

$R^2$ represents a hydrogen atom or a hydroxyl group, and preferably hydrogen atom.

$R^3$ represents —$CH_2$—, —$CH(OH)$—$CH_2$— or —$CH$=$CH$—, preferably —$CH_2$— or —$CH(OH)$—$CH_2$—, and most preferably —$CH(OH)$—$CH_2$—.

$R^4$ represents a hydrogen atom or $CH_3$, preferably hydrogen atom.

x is zero to 35, preferably zero to 26, more preferably eleven to 26, even more preferably eleven to 23 and most preferably eighteen to 23.

y and z represent the integers that satisfy y+z=zero to three. Here, —$(CH_2)_y(CH(CH_3))_z$— does not mean that ($CH_2$) and ($CH(CH_3)$) are aligned in this order but only indicates simply a quantitative relationship. For example, —(CH$_2$)$_y$(CH(CH$_3$))$_z$— represents one of —CH(CH$_3$)CH$_2$CH$_2$—, —CH$_2$CH(CH$_3$)CH$_2$— or —CH$_2$CH$_2$CH(CH$_3$)— when y=2 and z=1. In addition, y and z are preferably z=0 and y=0-3, and more preferably z=0 and y=1-3.

The present invention is to provide a medicine comprising these glycolipids as active ingredients for treatment of an autoimmune disease. In addition, it is to provide a medicine comprising these glycolipids as active ingredients for treatment of diseases wherein the Th1/Th2 immune balance is shifted toward Th1 bias or diseases wherein Th1 cells aggravate the pathologic conditions. Furthermore, the present invention is to provide a selective IL-4 production inducing agent comprising these glycolipids as active ingredients.

DETAILED DESCRIPTION OF THE INVENTION

Figure 1:
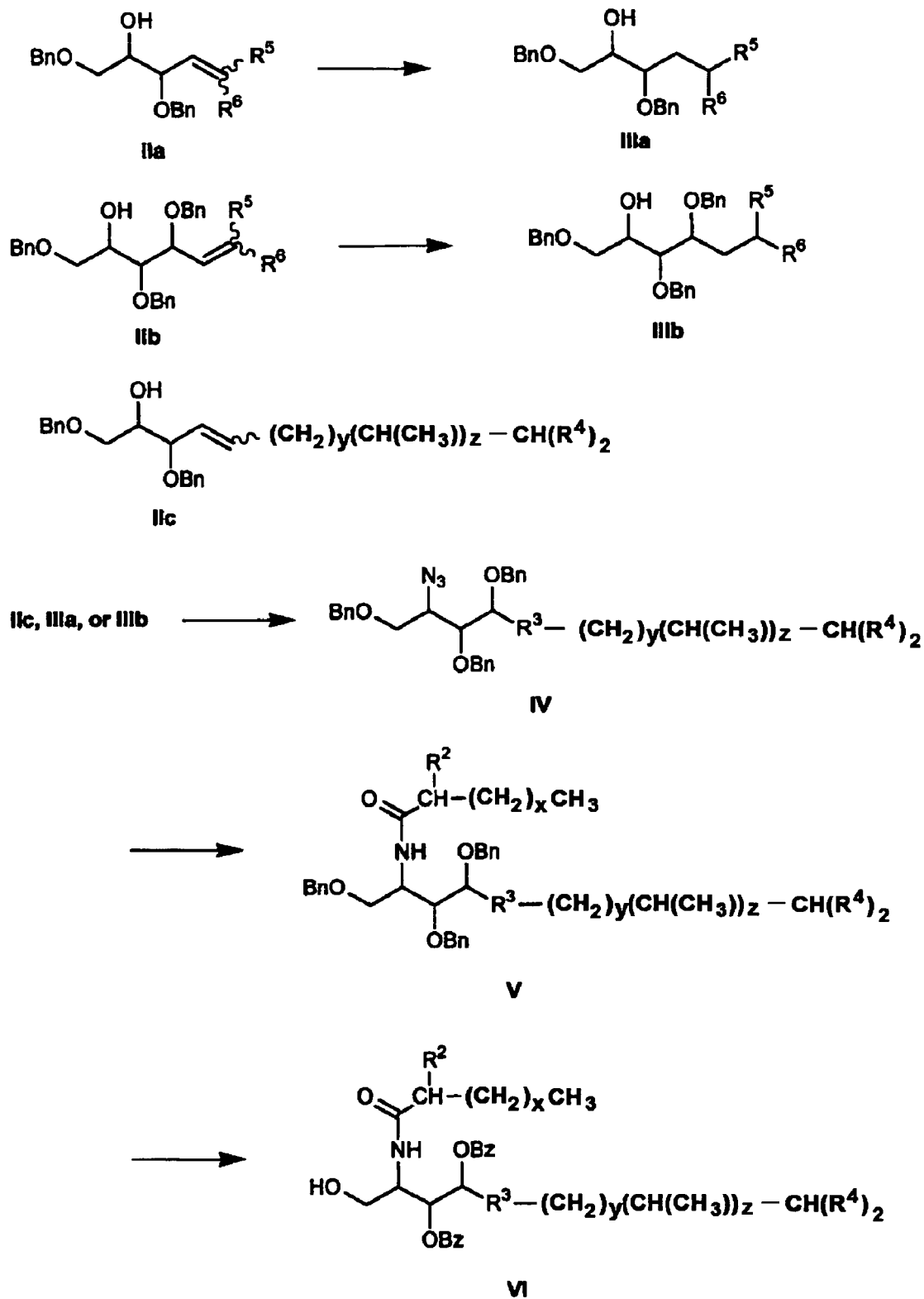
FIGS. 1 and 2 shown an example of a production process for a glycolipid [Formula (I)] of the present invention. In the figure, R$^1$ represents an aldopyranose group, R$^2$ represents a hydrogen atom or a hydroxyl group, R$^3$ represents —CH$_2$—, —CH(OH)—CH$_2$— or —CH=CH—, R$^4$ represents hydrogen atom or methyl group, x represents an integer of zero to 35, y+z is an integer of zero to three, R5 represents hydrogen atom, methyl group or —(CH2)$_{y'}$—CH(CH$_3$))$_{z'}$—CH(R$_4$)$_2$ (where y'+z' is an integer of zero to two), R$^6$ represents hydrogen atom or methyl group and R$^7$ represents an adlopyranose in which the functional groups such as hydroxyl groups and amino groups are appropriately protected.

Autoimmune diseases can be divided into generalized autoimmune diseases and organ specific autoimmune diseases. Of these, organ specific autoimmune diseases cause chronic inflammation in specific organs or tissues (brain, liver, eyes and joints), and the cause is attributed to an immune response (an autoimmune response) to autoantigens specific to each organ. Multiple sclerosis (affecting brain and spinal cord) and rheumatoid arthritis (affecting joints) are typical examples of the disease. These diseases share many common characteristics although the affected organs are different, and the treatment methods also contain basic commonalities. In many of them, the T cells that produce IFN-γ play an important role.

NKT cells are lymphocytes having the properties of both NK and T cells and recognize the glycolipids bound to CD1d molecules through T cell antigen receptors.

NKT cells express physiological functions such as (a) anti-tumor activity (tumor cell eliminating effect), (b) IFN-γ production and (c) IL-4 production as well as (d) a function to enhance NK cell activity and (e) to activate macrophage. Both (d) and (e) are induced by the IFN-γ produced. That is, (a), (b) and (c) are direct actions of NKT cells, and (d) and (e) are indirect actions induced through (b).

Conventional alpha-galactosylceramide is a very powerful immuno stimulator that activates NKT cells and induces all of the actions (a) through (e). Here, the conventional alpha-galactosylceramide refers to a material having a longer carbon chain than the glycolipid of the present invention in the sphingosine base. For example, it refers to the glycolipids used as comparisons in the examples described later as well as those described in Science, Vol. 278, pp. 1626-1629 (1997), Proc. National Academy Science USA Vol. 95, pp.5690-5693 (1998), Japanese Patent Application Public Disclosure (Kokai) Hei 5-9193, Japanese Patent Application Public Disclosure (Kokai) Hei 5-59081 and U.S. Pat. No. 5,936,076. Of the properties induced, (c) IL-4 production is effective in suppressing an autoimmune disease but (b) IFN-γ production aggravates the autoimmune disease thus canceling each other and making it ineffective in treating autoimmune diseases. In addition, corresponding numbers of NKT cell stimulated by the conventional alpha-galactosylceramide are instantly decimated through apoptosis. In contrast, the glycolipids of the present invention have a weaker immune activation effect than the conventional alpha-galactosylceramide and selectively induce (c) IL-4 production of the NKT cell functions. Since IFN-γ derivation is avoided, the glycolipids of the present invention can deliver the effect to suppress and treat organ specific autoimmune diseases. In addition, the glycolipids of the present invention are superior in that they do not induce NKT cell apoptosis.

The research on the interactions among NKT cell antigen receptors, glycolipids and CD1d molecules is progressing in recent years. (See Immunological Review Journal, 1999, Vol. 172, pp. 285-296.) Currently, the two hydrophobic carbon chain segments derived from the sphingosine base and a fatty acid of a glycolipid are thought to burrow deep into the two trenches (pockets) in a CD1d molecule to make a connection and the hydrophilic glycosyl segment is thought to bond with a NKT cell antigen receptor. The carbon chain in a sphingosine base in an glycolipid of the present invention is shorter than that of conventional alpha-galactosylceramide, and the bond to a CD1d molecule is weaker. As a result, the glycosyl segment stability declines and the nature of the signal transmitted to antigen receptors is modified. Another result induced is selective IL-4 production. The effect of glycolipids of the present invention does not correspond to that of alpha-galactosylceramide at any dosage, and they are concluded to be substantially different ligands. [Refer to the examples described later and a published thesis. (Nature, Vol. 413, No. 6855, pp. 531-534 (2001).]

The glycolipids of the present invention are represented by the formula (I) above. For example, (1) (2S, 3S, 4R)-1-O-(α-D-galactosyl)-2—(N-triacontanoyl amino)-1,3,4-heptane triol, (2) (2S, 3S, 4R)-1-O-(α-D-galactosyl)-2—(N-nonacosanoyl amino)-1,3,4-heptane triol, (3) (2S, 3S, 4R)-1-O-(α-D-galactosyl)-2—(N-octacosanoyl amino)-1,3,4-heptane triol, (4) (2S, 3S, 4R)-1-O-(α-D-galactosyl)-2—(N-heptacosanoyl amino)-1,3,4-heptane triol, (5) (2S, 3S, 4R)-1-O-(α-D-galactosyl)-2—(N-hexacosanoyl amino)-1,3,4-heptane triol, (6) (2S, 3S, 4R)-1-O-(α-D-galactosyl)-2-(N-pentacosanoyl amino)-1,3,4-heptane triol, (7) (2S, 3S, 4R)-1-O-(α-D-galactosyl)-2-(N-tetracosanoyl amino)-1,3,4-heptane triol, (8) (2S, 3S, 4R)-1-O-(α-D-galactosyl)-2-(N-tricosanoyl amino)-1,3,4-heptane triol, (9) (2S, 3S, 4R)-1-O-(α-D-galactosyl)-2-(N-docosanoyl amino)-1,3,4-heptane triol, (10) (2S, 3S, 4R)-1-O-(α-D-galactosyl)-2-(N-heneicosanoyl amino)-1,3,4-heptane triol, (11) (2S, 3S, 4R)-1-O-(α-D-galactosyl)-2-(N-eicosanoyl amino)-1,3,4-heptane triol, (12) (2S, 3S, 4R)-1-O-(α-D-galactosyl)-2-(N-nonadecanoyl amino)-1,3,4-heptane triol, (13) (2S, 3S, 4R)-1-O-(α-D-galactosyl)-2-(N-triacontanoyl amino)-1,3,4-octane triol, (14) (2S, 3S, 4R)-1-O-(α-D-galactosyl)-2-(N-nonacosanoyl amino)-1,3,4-octane triol, (15) (2S, 3S, 4R)-1-O-(α-D-galactosyl)-2-(N-octacosanoyl amino)-1,3,4-octane triol, (16) (2S, 3S, 4R)-1-O-(α-D-galactosyl)-2-(N-heaptacosanoyl amino)-1,3,4-octane triol, (17) (2S, 3S, 4R)-1-O-(α-D-galactosyl)-2-(N-hexacosanoyl amino)-1,3,4-octane triol, (18) (2S, 3S, 4R)-1-O-(α-D-galactosyl)-2-(N-pentacosanoyl amino)-1,3,4-octane triol, (19) (2S, 3S, 4R)-1-O-(α-D-galactosyl)-2-(N-tetracosanoyl amino)-1,3,4-octane triol, (20) (2S, 3S, 4R)-1-O-(α-D-galactosyl)-2-(N-tricosanoyl amino)-1,3,4-octane triol, (21) (2S, 3S, 4R)-1-O-(α-D-galactosyl)-2-(N-docosanoyl amino)-1,3,4-octane triol, (22) (2S, 3S, 4R)-1-O-(α-D-galactosyl)-2-(N-heneicosanoyl amino)-1,3,4-octane triol, (23) (2S, 3S, 4R)-1-O-(α-D-galactosyl)-2-(N-eicosanoyl amino)-1,3,4-octane triol, (24) (2S, 3S, 4R)-1-O-(α-D-galactosyl)-2-(N-nonadecanoyl amino)-1,3,4-octane triol, (25) (2S, 3S, 4R)-1-O-(α-D-galactosyl)-2-(N-triacontanoyl amino)-1,3,4-nonane triol, (26) (2S, 3S, 4R)-1-O-(α-D-galactosyl)-2-(N-nonacosanoyl amino)-1,3,4-nonane triol, (27) (2S, 3S, 4R)-1-O-(α-D-galactosyl)-2-(N-octacosanoyl amino)-1,3,4-nonane triol, (28) (2S, 3S, 4R)-1-O-(α-D-galactosyl)-2-(N-heptacosanoyl amino)-1,3,4-nonane triol, (29) (2S, 3S, 4R)-1-O-(α-D-galactosyl)-2-(N-hexacosanoyl amino)-1,3,4-nonane triol, (30) (2S, 3S, 4R)-1-O-(α-D-galactosyl)-2-(N-pentacosanoyl amino)-1,3,4-nonane triol, (31) (2S, 3S, 4R)-1-O-(α-D-galactosyl)-2-(N-tetracosanoyl amino)-1,3,4-nonane triol, (32) (2S, 3S, 4R)-1-O-(α-D-galactosyl)-2-(N-tricosanoyl amino)-1,3,4-nonane triol, (33) (2S, 3S, 4R)-1-O-(α-D-galactosyl)-2-(N-docosanoyl amino)-1,3,4-nonane triol, (34) (2S, 3S, 4R)-1-O-(α-D-galactosyl)-2-(N-heneicosanoyl amino)-1,3,4-nonane triol, (35) (2S, 3S, 4R)-1-O-(α-D-galactosyl)-2-(N-eicosanoyl amino)-1,3,4-nonane triol, (36) (2S, 3S, 4R)-1-O-(α-D-galactosyl)-2-(N-nonadecanoyl amino)-1,3,4-nonane triol, (37) (2S, 3S, 4R)-1-O-(α-D-galactosyl)-2-(N-triacontanoyl amino)-1,3,4-hexane triol, (38) (2S, 3S, 4R)-1-O-(α-D-galactosyl)-2-(N-nonacosanoyl amino)-1,3,4-hexane triol, (39) (2S, 3S, 4R)-1-O-(α-D-galactosyl)-2-(N-octacosanoyl amino)-1,3,4-hexane triol, (40) (2S, 3S, 4R)-1-O-(α-D-galactosyl)-2-(N-heptacosanoyl amino)-1,3,4-hexane triol, (41) (2S, 3S, 4R)-1-O-(α-D-galactosyl)-2-(N-hexacosanoyl amino)-1,3,4-hexane triol, (42) (2S, 3S, 4R)-1-O-(α-D-galactosyl)-2-(N-pentacosanoyl amino)-1,3,4-hexane triol, (43) (2S, 3S, 4R)-1-O-(α-D-galactosyl)-2-(N-tetracosanoyl amino)-1,3,4-hexane triol, (44) (2S, 3S, 4R)-1-O-(α-D-galactosyl)-2-(N-tricosanoyl amino)-1,3,4-hexane triol, (45) (2S, 3S, 4R)-1-O-(α-D-galactosyl)-2-(N-docosanoyl amino)-1,3,4-hexane triol, (46) (2S, 3S, 4R)-1-O-(α-D-galactosyl)-2-(N-heneicosanoyl amino)-1,3,4-hexane triol, (47) (2S, 3S, 4R)-1-O-(α-D-galactosyl)-2-(N-eicosanoyl amino)-1,3,4-hexane triol and (48) (2S, 3S, 4R)-1-O-(α-D-galactosyl)-2-(N-nonadacanoyl amino)-1,3,4-hexane triol can be mentioned. Of these, (3) to (9), (15) to (21), (27) to (33) and (39) to (45) are preferred.

Figure 2:
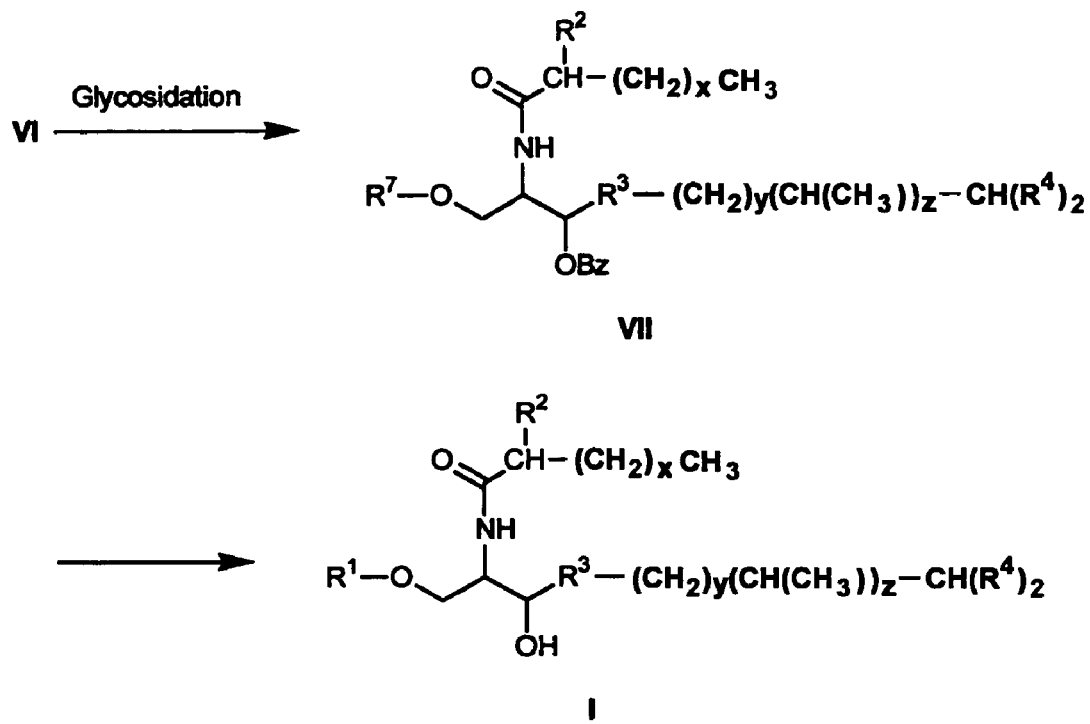

The glycolipids of the present invention can be manufactured using various methods, but they can be manufactured according to the method, for example, described below. The production process is shown in FIGS. 1 and 2. That is, compounds (IIa), (IIb) and (IIc) are obtained according to the method described in a publication (M. Morita et al., J. Med. Chem., 1995, 38, 2176 and the like), and the double bond segments of (IIa) and (IIb) are reduced to convert them into compounds (IIIa) and (IIIb). After mesylating or tosylating the secondary hydroxyl group of the compounds (IIIa), (IIIb) and (IIc), compound (IV) is obtained upon converting them into azide groups and compound (V) is obtained through a selective reduction of the azide group into an amino group and a subsequent amide formation reaction. Compound (VI) is obtained by simultaneously converting the benzyl group present in compound (V) as a protective group for the secondary hydroxyl group into an acyl group such as a benzoyl group and an acetyl group and removing the protection from the primary hydroxyl group. Compound (VI) is glycosylated to obtain compound (VII), and the desired compound (I) can be obtained by removing the remaining protective groups.

The glycolipids of the present invention can be used as medicines for autoimmune diseases, medicines for diseases wherein Th1/Th2 immune balance is shifted toward Th1 bias or medicines for diseases in which Th1 cells aggravate pathologic conditions and also as selective IL-4 production inducing agents. Here, autoimmune diseases signifies multiple sclerosis, rheumatoid arthritis, psoriasis, Crohn's disease, vitiligo vulgaris, Behcet's disease, collagen diseases, Type 1 diabetes, uveitis, Sjogren's syndrome, autoimmune type myocarditis, autoimmune liver diseases, autoimmune gastritis, pemphigus, Guillain-Barre syndrome, HTLV-1 associated myelopathy and the like. In addition, diseases in which the Th1/Th2 immune balance is shifted toward Th1 bias signifies autoimmune diseases such as multiple sclerosis, rheumatoid arthritis, psoriasis, Type 1 diabetes, uveitis, Sjogren's syndrome and the like as well as diseases associated with cell immunology such as acute hepatitis, transplant rejection, infections caused by intra-cellular infectious pathogens and the like.

The glycolipids [Formula (I)] of the present invention have low toxicity. For example, all ten groups of five week old mice survived, which received 300 μg/kg intra peritoneal administration of compound 25 twice a week for four months in an experiment. The glycolipids (I) of the present invention may be administered alone, but, when desired, they can also be used along with well known carriers ordinarily tolerated pharmacologically in formulations targeted to improve and treat the symptoms caused by autoimmune diseases or diseases shifting the Th1/Th2 immune balance toward Th1 bias or diseases the pathologic conditions of which is aggravated by Th1 cells. For example, the active ingredient may be administered orally or non-orally by itself or along with a commonly used vehicle upon appropriately forming into capsules, tablets or injection agents. Capsules, for example, are prepared by mixing a stock powder with a vehicle such as lactose, starch or derivatives thereof, cellulose derivatives and the like and packing into gelatin capsules. In addition to the aforementioned vehicle, a binding agent such as carboxymethylcellulose sodium salt, alginic acid, gum Arabic and the like and water are added to the active ingredient, the mixture is kneaded and granulated as necessary before adding a lubricant such as talc and Stearic acid, and tablets are formed using an ordinary compression stamping machine. For injection, when injected a non-oral administration, is used, an active ingredient is dissolved along with a dissolution aid in sterilized distilled water or sterilized physiological saline solution and sealed in ampoules to yield an injection formulation. A stabilizer and a buffering substance may be present when necessary.

The dosage for the pharmaceutical improvement and medicines of the present invention for autoimmune diseases, diseases in which Th1/Th2 immune balance is shifted toward Th1 bias and IL-4 inducing agents depends on various factors such as, for example, the patient's symptoms and age, the path of administration, the formulation type and the number of administrations. However, 0.001 mg to 5,000 mg/day/person is ordinarily suitable with 0.01 mg to 500 mg/day/person preferred and 0.5 mg to 100 mg/day/person more preferred.

Effect of the Invention

The glycolipids of the present invention are the first medicine that treats autoimmune diseases by effectively stimulating the immune adjusting capability of NKT cells. In addition, the glycolipids of the present invention are the first glycolipids proven to have an autoimmune disease suppressing effect. Furthermore, the glycolipids of the present invention are extremely revolutionary medicines based on the fact that they selectively induce only the autoimmune disease treatment function of NKT cells.

The glycolipids of the present invention can be used immediately as medicines for autoimmune diseases that could be suppressed by IL-4 levels. In addition, IL-4 acts to enhance antibody production and can be used as an aid in vaccine treatment. Furthermore, the glycolipids of the present invention are thought to be effective when administered in combination with, for example, hepatitis virus vaccine to patients having difficulties raising their antibody levels. The glycolipids of the present invention can also be used on diseases in which NKT cell functions are depressed.

The present invention is illustrated using the examples shown below, but the examples are not intended to limit the present invention.

REFERENCE EXAMPLE 1

Synthesis of (2R,3S,4R)-1,3,4-tri-O-benzyl-5-octene-1,2,3,4-tetraol (Compound 1)

$NaIO_4$ (760 mg) was added to a solution of 3,4,6-tri-O-benzyl-D-galactose (0.99 g) in ethanol/water (4/1, 12.5 ml) at 0° C. The resulting mixture was stirred for six hours at room temperature. The mixture was diluted with methylene chloride, and water was added to separate the solution. The aqueous layer was extracted twice with methylene chloride. The organic layer was dried with $MgSO_4$, and the solvent was removed under reduced pressure. A solution of the crude oil in THF (6 ml) was added dropwise at −10° C. to a separately prepared solution of propylidene (triphenyl) phosphorane (5 mmoles) in THF-hexane (11.2 ml), and the resulting mixture was stirred for 22 hours at room temperature. A mixed solvent of MeOH/$H_2O$ (4/1, 50 ml) was added and extracted four times with hexane, the organic phase was dried with $Na_2SO_4$, and the solvent was removed under reduced pressure. The resulting oil was purified by a silica gel column, and 270 mg of the title compound was obtained.

$^1$H-NMR (CDCl$_3$): 0.92 (t, J=8 Hz, 3H), 1.85-2.05 (m, 2H), 2.97 (d, J=5 Hz, 1H), 3.51 (d, J=6 Hz, 2H), 3.55-3.60 (m, 1H), 4.05-4.10 (m, 1H), 4.35 (d, J=12 Hz, 1H), 4.40-4.50 (m, 1H), 4.50-4.55 (m, 3H), 4.60 (d, J=12 Hz, 1H), 4.69 (d, J=12 Hz, 1H), 5.44 (t, J=10 Hz, 1H), 5.70-5.80 (m, 1H), 7.2-7.4 (m, 15H).

REFERENCE EXAMPLE 2

Synthesis of (2R,3S,4R)-1,3,4-tri-O-benzyl-5-heptene-1,2,3,4-triol (Compound 2)

The title compound was obtained using 3,4,6-tri-O-benzyl-D-galactose and ethylidene (triphenyl) phosphorane in the same procedure for the synthesis of compound 1.

$^1$H-NMR (CDCl$_3$): 1.57 (dd, J=7 Hz and 2 Hz, 3H), 2.95 (d, J=5 Hz, 1H), 3.52 (d, J=6 Hz, 2H), 3.55-3.60 (m, 1H), 4.05-4.10 (m, 1H), 4.35 (d, J=12 Hz, 1H), 4.40-4.55 (m, 3H), 4.60 (d, J=12 Hz, 1H), 4.69 (d, J=12 Hz, 1H), 5.51 (t, J=10 Hz, 1H), 5.80-5.90 (m, 1H), 7.2-7.4 (m, 15H).

REFERENCE EXAMPLE 3

Synthesis of (2R,3S,4R)-1,3,4-tri-O-benzyl-5-nonene-1,2,3,4-tetraol (Compound 3)

The title compound was obtained using 3,4,6-tri-O-benzyl-D-galactose and butylidene (triphenyl) phosphorane in the same procedure for the synthesis of compound 1.

$^1$H-NMR (CDCl$_3$): 0.90 (t, J=7 Hz, 3H), 1.35-1.42 (m, 2H), 1.87-2.04 (m, 2H), 3.05 (d, J=5 Hz, 1H), 3.55 (d, J=6 Hz, 2H), 3.60-3.62 (m, 1H), 4.10-4.12 (m, 1H), 4.38 (d, J=12 Hz, 1H), 4.45-4.56 (m, 4H), 4.64 (d, J=12 Hz, 1H), 4.72 (d, J=12 Hz, 1H), 5.51 (t, J=10 Hz), 7.26-7.36 (m, 15H).

REFERENCE EXAMPLE 4

Synthesis of (2R,3S,4R)-1,3,4-tri-O-benzyl-1,2,3,4-octane tetraol (Compound 4)

To a solution of compound 1 (270 mg) in THF (3 ml) was added 10% Pd—C (30 mg), and the resulting mixture was stirred at room temperature for an hour under a hydrogen atmosphere. The title compound (262 mg) was obtained by removing the catalyst through filtration and removing the solvent.

$^1$H-NMR (CDCl$_3$): 0.88 (t, J=3 Hz, 3H), 1.25-1.75 (m, 6H), 3.15 (d, J=5 Hz, 1H), 3.5-3.7 (m, 4H), 4.05-4.10 (m, 1H), 4.50-4.75 (m, 6H), 7.25-7.40 (m, 15H).

REFERENCE EXAMPLE 5

Synthesis of (2S,3S,4R)-2-azide-1,3,4-tri-O-benzyl-1,3,4-octanet triol (Compound 5)

Triethylamine (240 μl) and methane sulfonyl chloride (108 μl) were consecutively added to a solution of compound 4 (262 mg) in pyridine at room temperature following which the mixture was stirred for an hour at room temperature. The mixture was extracted with ether and was dried with anhydrous sodium sulfate after washing the organic layer with saturated potassium bisulfate, water, aqueous sodium bicarbonate solution and brine. The solvent was evaporated under reduced pressure, and 282 mg of residue was obtained. The residue was dissolved in DMF (2 ml), and NaN$_3$ (0.3 g) was added. The mixture was stirred for 24 hours at 100° C. and was diluted with ethyl acetate. The organic layer was washed with water and dried with anhydrous sodium sulfate. The solvent was evaporated, and the residue was purified by flash chromatography (hexane/ethyl acetate=100/0 to 90/10) to obtain 200 mg of the title compound.
$^1$H-NMR (CDCl$_3$): 0.89 (t, J=7 Hz, 3H), 1.25-1.80 (m, 6H), 3.60-3.85 (m, 5H), 4.45-4.75 (m, 6H), 7.25-7.40 (m, 15H).

REFERENCE EXAMPLE 6

Synthesis of (2S,3S,4R)-2-azide-1,3,4-tri-O-benzyl-1,3,4-heptane triol (Compound 6)

After compound 2 was used in the same procedure for the synthesis of compound 4, the title compound was subsequently obtained by the same procedure in the synthesis of compound 5.
$^1$H-NMR (CDCl$_3$): 0.90 (t, J=7 Hz, 3H), 1.30-1.75 (m, 4H), 3.60-3.85 (m, 5H), 4.50-4.75 (m, 6H), 7.25-7.40 (m, 15H).

REFERENCE EXAMPLE 7

Synthesis of (2S,3S,4R)-2-azide-1,3,4-tri-O-benzyl-1,3,4-nonane triol (Compound 7)

After compound 3 was used in the same procedure for the synthesis of compound 4, the title compound was subsequently obtained by the same procedure in the synthesis of compound 5.
$^1$H-NMR (CDCl$_3$): 0.88 (t, J=7 Hz, 3H), 1.20-1.72 (m, 8H), 3.59-3.72 (m, 5H), 4.50-4.80 (m, 6H), 7.27-7.36 (m, 15H).

REFERENCE EXAMPLE 8

Synthesis of (2S,3S,4R)-2-(N-tetracosanoyl amino)-1,3,4-tri-O-benzyl-1,3,4-octane triol (Compound 8)

To a solution of compound 5 (200 mg) in THF (7 ml) was added 10% Pd—C (20 mg). The resulting mixture was stirred for fourteen hours at room temperature under a hydrogen atmosphere. The catalyst was filtered with a membrane filter, and the solvent was removed under reduced pressure. The residue was dissolved in methylene chloride (5 ml), and tetracosanoic acid, 1-methyl-2-chloropyridineum iodide (252 mg) and tributylamine (136 μl) were consecutively added. The resulting mixture was stirred for 2.5 hours while heating. After adding ethyl acetate to the reaction mixture, the mixture was washed with 5% aqueous sodium thiosulfate solution and aqueous saturated potassium hydrogen sulfate solution. The organic layer was dried with sodium sulfate and was then purified by flash chromatography (acetone/hexane=4/96 to 1/4) to obtain 213 mg of the title compound.
$^1$H-NMR (CDCl$_3$): 0.80 (m, 6H), 1.20-1.75 (m, 48H), 2.0-2.1 (m, 2H), 3.45-3.55 (m, 2H), 3.75-3.85 (m, 2H), 4.20-4.30 (m, 1H), 4.44 (s, 2H), 4.45-4.60 (m, 3H), 4.82 (d, J=11 Hz, 1H), 5.78 (d, J=9 Hz, 1H), 7.25-7.40 (m, 15H).

REFERENCE EXAMPLE 9

Synthesis of (2S,3S,4R)-2-(N-tetracosanoyl amino)-1,3,4-tri-O-benzyl-1,3,4-heptane triol (Compound 9)

Compound 6 was used in the same procedure for the synthesis of compound 8, and the title compound was obtained.
$^1$H-NMR (CDCl$_3$): 0.85-0.95 (m, 6H), 1.20-1.75 (m, 46H), 2.0-2.1 (m, 2H), 3.50-3.55 (m, 2H), 3.80-3.85 (m, 2H), 4.20-4.30 (m, 1H), 4.46 (s, 2H), 4.50-4.65 (m, 3H), 4.83 (d, J=11 Hz, 1H), 5.77 (d, J=9 Hz, 1H), 7.25-7.40 (m, 15H).

REFERENCE EXAMPLE 10

Synthesis of (2S,3S,4R)-2-(N-tetracosanoyl amino)-1,3,4-tri-O-benzyl-1,3,4-heptane triol (Compound 10)

Compound 7 was used in the same procedure for the synthesis of compound 8, and the title compound was obtained.
$^1$H-NMR (CDCl$_3$): 0.85-0.95 (m, 6H), 1.26-1.70 (m, 50H), 2.00-2.05 (m, 2H), 3.49-3.54 (m, 2H), 3.79-3.83 (m, 2H), 4.22-4.28 (m, 2H), 4.45 (s, 1H), 4.49-4.54 (m, 2H), 4.59 (d, J=12 Hz, 1H), 4.82 (d, J=12 Hz, 1H), 5.76 (d, J=9 Hz, 1H), 7.26-7.34 (m, 15H).

REFERENCE EXAMPLE 11

Synthesis of (2S,3S,4R)-2-(N-tetracosanoyl amino)-3,4-di-O-benzoyl-1-O-triphenyl methyl-1,3,4-octane triol (Compound 11)

A mixture of compound 8 (210 mg), Pd—C (10%, 60 mg) and PdCl$_2$ (30 mg) in ethyl acetate (10 ml) was stirred for 30 minutes at room temperature under a hydrogen atmosphere. THF-EtOH (1/1; 25 ml) was added, and the solvent was evaporated after the catalyst was removed. Triphenyl methyl chloride (587 mg) and dimethyl aminopyridine (20 mg) were added to the residue in pyridine (1.7 ml), and the mixture was stirred for nine hours at 40° C. Pyridine was removed under reduced pressure, and the residue was purified by flash chromatography (methylene chloride/acetone=100/0 to 50/1) to give a fraction containing a diol derivative. The solvent was removed and to the residue were added pyridine (2 ml), dimethylamino pyridine (25 mg) and benzoyl chloride (200 μl). The mixture was stirred for 66 hours at 40° C. The solvent was removed under reduced pressure, and the residue was purified by flash chromatography (hexane/ethyl acetate=98/2 to 80/20) to obtain 128 mg of the title compound.
$^1$H-NMR (CDCl$_3$): 0.80-0.95 (m, 6H), 1.20-1.45 (m, 44H), 1.5-2.0 (m, 4H), 2.1-2.3 (m, 2H), 3.25-3.35 (m, 2H), 4.5-4.65 (m, 1H), 5.30-5.35 (m, 1H), 5.79 (dd, J=2 Hz and 9 Hz, 1H), 5.99 (d, J=9 Hz, 1H), 7.05-7.35 (m, 15H), 7.35-7.60 (m, 6H), 7.88 (d, J=7 Hz, 2H), 7.95-8.0 (m, 2H).

REFERENCE EXAMPLE 12

Synthesis of (2S,3S,4R)-2-(N-tetracosanoyl amino)-3,4-di-O-benzoyl-1-O-triphenyl methyl-1,3,4-heptane triol (Compound 12)

Compound 9 was used in the same procedure for the synthesis of compound 11, and the title compound was obtained.
$^1$H-NMR (CDCl$_3$): 0.85-0.95 (m, 6H), 1.20-1.50 (m, 42H), 1.55-1.75 (m, 2H), 1.80-1.95 (m, 2H), 2.1-2.3 (m, 2H), 3.30-3.40 (m, 2H), 4.55-4.65 (m, 1H), 5.35-5.40 (m, 1H), 5.82 (dd, J=2 Hz and 9 Hz, 1H), 6.13 (d, J=9 Hz, 1H), 7.05-7.65 (m, 21H), 7.89 (d, J=8 Hz, 2H), 7.89 (d, J=8 Hz, 2H), 7.96 (d, J=8 Hz, 2H).

REFERENCE EXAMPLE 13

Synthesis of (2S,3S,4R)-2-(N-tetracosanoyl amino)-3,4-di-O-benzoyl-1-O-triphenyl methyl-1,3,4-nonane triol (Compound 13)

Compound 10 was used in the same procedure for the synthesis of compound 11, and the title compound was obtained.
$^1$H-NMR (CDCl$_3$): 0.82-0.90 (m, 6H), 1.26-1.41 (m, 46H), 1.60-1.65 (m, 2H), 1.74-1.89 (m, 2H), 2.14-2.24 (m, 2H), 3.27-3.35 (m, 2H), 4.56-4.60 (m, 1H), 5.34-5.40 (m, 1H), 5.79 (dd, J=3 Hz and 9 Hz, 1H), 5.99 (d, J=9 Hz, 1H), 7.11-7.69 (m, 21H), 7.89 (d, J=8 Hz, 2H), 7.96 (d, J=7 Hz, 2H).

REFERENCE EXAMPLE 14

Synthesis of (2S,3S,4R)-2-(N-tetracosanoyl amino)-3,4-di-O-benzoyl-1,3,4-octane triol (Compound 14)

p-Toluene sulfonic acid monohydrate (14 mg) was added to a solution of compound 11 (128 mg) in methylene chloride/methanol (2/1) (1.8 ml), and the resulting mixture was stirred for two hours at 30° C. The solvent was removed under reduced pressure, and the residue was purified by flash chromatography (hexane/ethyl acetate=85/15 to 50/50) to obtain 54 mg of the title compound.

$^1$H-NMR (CDCl$_3$): 0.85-0.95 (m, 6H), 1.20-1.50 (m, 44H), 1.60-1.75 (m, 2H), 1.95-2.10 (m, 2H), 2.29 (t, J=8 Hz, 2H), 2.70-2.75 (m, 1H), 3.6-3.7 (m, 2H), 4.35-4.45 (m, 1H), 5.35-5.45 (m, 2H), 6.33 (d, J=9 Hz, 1H), 7.38 (t, J=8 Hz, 2H), 7.50-7.60 (m, 3H), 7.64 (t, J=7 Hz, 1H), 7.95-8.00 (m, 2H), 8.05-8.10 (m, 2H).

REFERENCE EXAMPLE 15

Synthesis of (2S,3S,4R)-2-(N-tetracosanoyl amino)-3,4-di-O-benzoyl-1,3,4-heptane triol (Compound 15)

Compound 12 was used in the same procedure for the synthesis of compound 14, and the title compound was obtained.

$^1$H-NMR (CDCl$_3$): 0.88 (t, J=7 Hz, 3H), 0.97 (t, J=7 Hz, 3H), 1.20-1.75 (m, 44H), 2.0-2.1 (m, 2H), 2.30 (t, J=8 Hz, 2H), 3.6-3.7 (m, 2H), 4.35-4.45 (m, 1H), 5.35-5.45 (m, 2H), 6.38 (d, J=9 Hz, 1H), 7.38 (t, J=8 Hz, 2H), 7.45-7.70 (m, 3H), 7.95 (d, J=7 Hz, 2H), 8.05-8.10 (m, 2H).

REFERENCE EXAMPLE 16

Synthesis of (2S,3S,4R)-2-(N-tetracosanoyl amino)-3,4-di-O-benzoyl-1,3,4-nonane triol (Compound 16)

Compound 13 was used in the same procedure for the synthesis of compound 14, and the title compound was obtained.

$^1$H-NMR (CDCl$_3$): 0.85-0.90 (m, 6H), 1.26-1.48 (m, 46H), 1.65-1.72 (m, 2H), 1.89-2.10 (m, 2H), 2.29 (t, J=8 Hz, 2H), 2.74-2.77 (m, 1H), 3.58-3.68 (m, 2H), 4.36-4.41 (m, 1H), 5.36-5.43 (m, 2H), 6.34 (d, J=9 Hz, 1H), 7.38 (t, J=7 Hz, 2H), 7.48-7.55 (m, 3H), 7.64 (t, J=7 Hz, 1H), 7.95 (d, J=7 Hz, 2H), 8.06 (d, J=7 Hz, 2H).

REFERENCE EXAMPLE 17

Synthesis of (2S,3S,4R)-2-(N-tetracosanoyl amino)-3,4-di-O-benzoyl-1-O-(2,3,4,6-tetra-O-benzyl-α-D-galactosyl)-1,3,4-octane triol (Compound 17)

A mixture of compound 14 (54 mg), stannous chloride (38 mg), silver perchlorate (46 mg), and molecular sieve (4A, 270 mg) in THF (2 ml) was stirred for an hour at room temperature. Tetra-O-benzyl galactosyl fluoride (70 mg) was added to the mixture, and the resulting mixture was stirred for 2.5 hours. Ethyl acetate and brine were added to the reaction mixture, and the solution layers were separated. The organic layer was dried with anhydrous sodium sulfate. The solvent was evaporated under reduced pressure, and the residue was purified by flash chromatography (hexane/ethyl acetate=95/5 to 75/25) to obtain 45 mg of the title compound.

$^1$H-NMR (CDCl$_3$): 0.75-0.90 (m, 6H), 1.15-1.45 (m, 44H), 1.55-1.70 (m, 2H), 1.80-1.85 (m, 2H), 2.16 (t, J=7 Hz, 2H), 3.30-3.35 (m, 1H), 3.50-3.55 (m, 1H), 3.6-3.65 (m, 1H), 3.8-4.1 (m, 5H), 4.40-4.90 (m, 10H), 5.35-5.45 (m, 1H), 5.70 (dd, J=10 Hz and 3 Hz, 1H), 7.01 (d, J=9 Hz, 1H), 7.15-7.60 (m, 26H), 7.90-7.95 (m, 2H), 8.00-8.05 (m, 2H).

REFERENCE EXAMPLE 18

Synthesis of (2S,3S,4R)-2-(N-tetracosanoyl amino)-3,4-di-O-benzoyl-1-O-(2,3,4,6-tetra-O-benzyl-α-D-galactosyl)-1,3,4-heptane triol (Compound 18)

Compound 15 was used in the same procedure for the synthesis of compound 17, and the title compound was obtained.

$^1$H-NMR (CDCl$_3$): 0.85-0.90 (m, 6H), 1.15-1.50 (m, 42H), 1.55-1.70 (m, 2H), 1.80-1.90 (m, 2H), 2.15 (t, J=7 Hz, 2H), 3.30-3.35 (m, 1H), 3.50-3.55 (m, 1H), 3.6-3.65 (m, 1H), 3.8-3.9 (m, 2H), 3.95-4.05 (m, 2H), 4.05-4.15 (m, 1H), 4.40-4.90 (m, 10H), 5.40-5.45 (m, 1H), 5.69 (dd, J=10 Hz and 3 Hz, 1H), 6.93 (d, J=9 Hz, 1H), 7.15-7.65 (m, 26H), 7.92 (d, J=7 Hz, 2H), 8.03 (d, J=7 Hz, 2H).

REFERENCE EXAMPLE 19

Synthesis of (2S,3S,4R)-2-(N-tetracosanoyl amino)-3,4-di-O-benzoyl-1-O-(2,3,4,6-tetra-O-benzyl-α-D-galactosyl)-1,3,4-nonane triol (Compound 19)

Compound 16 was used in the same procedure for the synthesis of compound 17, and the title compound was obtained.

$^1$H-NMR (CDCl$_3$): 0.87-0.90 (m, 6H), 1.25-1.37 (m, 46H), 1.61-1.64 (m, 2H), 1.78-1.91 (m, 2H), 2.16 (t, J=7 Hz, 2H), 3.30-3.35 (m, 1H), 3.45-3.54 (m, 1H), 3.60-3.64 (m, 1H), 3.82-3.87 (m, 2H), 3.94-4.10 (m, 3H), 4.35-4.93 (m, 10H), 5.39-5.43 (m, 1H), 5.70 (dd, J=9 Hz and 3 Hz, 1H), 7.01 (d, J=9 Hz, 1H), 7.16-7.38 (m, 22H), 7.45 (t, J=7 Hz, 2H), 7.52 (t, J=7 Hz, 1H), 7.60 (t, J=7 Hz, 1H), 7.93 (d, J=7 Hz, 2H), 8.03 (d, J=7 Hz, 2H).

REFERENCE EXAMPLE 20

Synthesis of (2S,3S,4R)-3,4-di-O-benzoyl-1-O-(α-D-galactosyl)-2-(N-tetracosanoyl amino)-1,3,4-octane triol (Compound 20)

A mixture of compound 17 (45 mg), Pd—C (10%, 12 mg) and PdCl$_2$ (12 mg) in ethyl acetate (3 ml) was stirred for 1.5 hours at room temperature under a hydrogen atmosphere. The catalyst was filtered, and the solvent was removed under reduced pressure. The residue was purified by flash chromatography (acetone/hexane=2/3), and 24 mg of the title compound was obtained.

$^1$H-NMR (CDCl$_3$): 0.80-0.90 (m, 6H), 1.20-1.50 (m, 44H), 1.60-1.75 (m, 2H), 1.90-2.00 (m, 2H), 2.25-2.35 (m, 3H), 2.68 (s, 1H), 2.88 (s, 1H), 3.43 (br t, 1H), 3.65-4.05 (m, 8H), 4.60 (br t, 1H), 4.79 (d, J=4 Hz, 1H), 5.20-5.25 (m, 1H), 5.77 (dd, J=10 Hz and 3 Hz, 1H), 7.35-7.65 (m, 7H), 7.90-7.95 (m, 2H), 8.00-8.05 (m, 2H).

REFERENCE EXAMPLE 21

Synthesis of (2S,3S,4R)-3,4-di-O-benzoyl-1-O-(α-D-galactosyl)-2-(N-tetracosanoyl amino)-1,3,4-heptane triol (Compound 21)

Compound 18 was used in the same procedure for the synthesis of compound 20, and the title compound was obtained.

$^1$H-NMR (CDCl$_3$): 0.88 (t, J=7 Hz, 3H), 0.93 (t, J=7 Hz, 3H), 1.20-1.40 (m, 41H), 1.4-1.55 (m, 1H), 1.60-1.75 (m, 2H), 1.85-2.00 (m, 2H), 2.11 (d, J=10 Hz, 1H), 2.32 (t, J=8 Hz, 2H), 2.52 (s, 1H), 2.64 (s, 1H), 3.44 (br t, 1H), 3.65-4.05 (m, 8H), 4.60 (br t, 1H), 4.80 (d, J=4 Hz, 1H), 5.25-5.30 (m, 1H), 5.77 (dd, J=10 Hz and 3 Hz, 1H), 7.35-7.65 (m, 7H), 7.90-7.95 (m, 2H), 8.00-8.05 (m, 2H).

REFERENCE EXAMPLE 22

Synthesis of (2S,3S,4R)-3,4-di-O-benzoyl-1-O-(α-D-galactosyl)-2-(N-tetracosanoyl amino)-1,3,4-nonane triol (Compound 22)

Compound 19 was used in the same procedure for the synthesis of compound 20, and the title compound was obtained.

¹H-NMR (CDCl₃): 0.88-0.90 (m, 6H), 1.25-1.32 (m, 46H), 1.68-1.73 (m, 2H), 2.27-2.47 (m, 3H), 2.67 (s, 1H), 2.87 (s, 1H), 3.43 (t, J=7 Hz, 1H), 3.66-4.01 (m, 8H), 4.59 (t, J=10 Hz, 1H), 4.79 (d, J=4 Hz, 1H), 5.21-5.25 (m, 1H), 5.77 (dd, J=3 Hz and 10 Hz, 1H), 7.37-7.65 (m, 7H), 7.91 (d, J=7 Hz, 1H), 8.01 (d, J=7 Hz, 1H).

EXAMPLE 1

Synthesis of (2S,3S,4R)-1-O-(α-D-galactosyl)-2-(tetracosanoyl amino)-1,3,4-octane triol (Compound 23)

A 1M-sodium methoxide in methanol solution (250 μl) was added to a solution of compound 20 (24 mg) in MeOH-THF (1/1, 1.8 ml) at room temperature, and the resulting mixture was stirred for 30 minutes. AG 50W×8 (H+type) (430 mg) was added to the mixture, and the resulting mixture was stirred for ten minutes before the resin was filtered. The solvent was removed, and the residue was washed with a small amount of MeOH. A nitrogen gas stream was used to dry the product to obtain 15 mg of the title compound.
¹H-NMR (Pyridine-d₅): 0.80-0.90 (m, 6H), 1.15-1.45 (m, 42H), 1.55-1.70 (m, 1H), 1.75-1.90 (m, 4H), 2.20-2.30 (m, 1H), 2.42 (t, J=7 Hz, 2H), 3.20 (br t, 1H), 4.30 (br s, 1H), 4.35-4.50 (m, 4H), 4.50-4.60 (m, 2H), 4.60-4.70 (m, 2H), 5.20-5.30 (m, 1H), 5.57 (d, J=4 Hz 1H), 6.00-6.10 (m, 1H), 6.3 (br s, 1H), 6.4 (bf d, 1H), 6.55 (br s, 1H), 6.65 (br s, 1H), 6.95 (br s, 1H), 8.43 (d, J=8 Hz, 1H). MS (ESI) m/z: 690.5 (M+H⁺).

EXAMPLE 2

Synthesis of (2S,3S,4R)-1-O-(α-D-galactosyl)-2-(tetracosanoyl amino)-1,3,4-heptane triol (Compound 24)

Using compound 21 and the same procedure for the synthesis of compound 23, the title compound was obtained.
¹H-NMR (Pyridine-d₅): 0.87 (t, J=7 Hz, 3H), 0.95 (t, J=7 Hz, 3H), 1.15-1.40 (m, 40H), 1.57-1.75 (m, 1H), 1.75-1.90 (m, 4H), 2.15-2.25 (m, 1H), 2.42 (t, J=7 Hz, 2H), 4.30 (br s, 2H), 4.35-4.45 (m, 4H), 4.45-4.57 (m, 2H), 4.57-4.70 (m, 2H), 5.20-5.30 (m, 1H), 5.56 (d, J=4 Hz 1H), 6.00-6.05 (m, 1H), 6.25 (br s, 1H), 6.4 (bf d, 1H), 6.5 (br s, 1H), 6.6 (br s, 1H), 6.9 (br s, 1H), 8.38 (d, J=8 Hz, 1H). MS (ESI) m/z: 676.4 (M+H⁺).

EXAMPLE 3

Synthesis of (2S,3S,4R)-1-O-(α-D-galactosyl)-2-(tetracosanoyl amino)-1,3,4-nonane triol (Compound 25)

Using compound 22 and the same procedure for the synthesis of compound 23, compound 25 (represented by the structural formula below) was obtained.

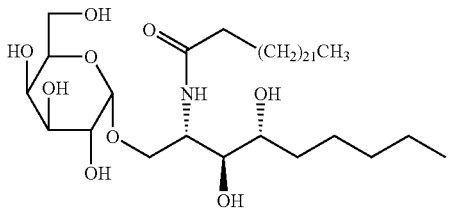

TLC: Rf=0.54 (CHCl₃:MeOH=3:1). ¹H-NMR (Pyridine-d₅): 0.80 (t, J=7 Hz, 3H), 0.86 (t, J=7 Hz, 3H), 1.22-1.31 (m, 44H), 1.58-1.69 (m, 1H), 1.79-1.84 (m, 4H), 2.20-2.30 (m, 1H), 2.43 (t, J=7 Hz, 2H), 4.29 (br s, 2H), 4.36-4.45 (m, 4H), 4.50-4.55 (m, 2H), 4.62-4.69 (m, 2H), 5.26 (d, J=5 Hz 1H), 5.57 (d, J=4 Hz, 1H), 6.04 (br s, 1H), 6.29 (br s, 1H), 6.39 (d, J=5 Hz, 1H), 6.51 (br s, 1H), 6.60 (br s, 1H), 6.93 (br s, 1H), 8.43 (d, J=9 Hz, 1H). MS (ESI) m/z: 704.5 (M+H⁺).

EXAMPLE 4

Synthesis of (2S,3S,4R)-1-O-(α-D-galactosyl)-2-(N-nonacosanoyl amino)-1,3,4-nonane triol (Compound 26)

The title compound was obtained using compound 7 and nonacosanoic acid by the same procedure for the synthesis of compounds 8, 14, 17, 20 and 23.
TLC: Rf=0.24 (CH₂Cl₂:MeOH=3:1). ¹H-NMR (CDCl₃:CD₃D=3:1): 7.34 (br s, 1H), 4.91 (d, 1H, J=3.5 Hz), 4.17 (m, 1H), 3.95-3.88 (m, 2H), 3.80-3.68 (m, 6H), 3.67-3.55 (m, 2H), 2.21 (t, 2H, J=7 Hz), 1.67-1.26 (m, 60H), 0.91-0.87 (m, 6H). MS (FAB) m/z: 774 (M+).

EXAMPLE 5

Synthesis of (2S,3S,4R)-1-O-(α-D-galactosyl)-2-(N-octacosanoyl amino)-1,3,4-nonane triol (Compound 27)

The title compound was obtained using compound 7 and octacosanoic acid by the same procedure for the synthesis of compounds 8, 14, 17, 20 and 23.
TLC: Rf=0.24 (CH₂Cl₂:MeOH=3:1). ¹H-NMR (CDCl₃:CD₃OD=3:1): 4.92 (d, 1H, J=3.7 Hz), 4.20-4.19 (m, 1H), 3.96-3.88 (m, 2H), 3.81-3.67 (m, 6H), 3.56-3.50 (m, 2H), 2.20 (t, 2H, J=7 Hz), 1.67-1.26 (m, 58H), 0.91-0.86 (m, 6H). MS (FAB) m/z: 760 (M+).

EXAMPLE 6

Synthesis of (2S,3S,4R)-1-O-(α-D-galactosyl)-2-(N-heptacosanoyl amino)-1,3,4-nonane triol (Compound 28)

The title compound was obtained using compound 7 and heptacosanoic acid by the same procedure for the synthesis of compounds 8, 14, 17, 20 and 23.
TLC: Rf=0.25 (CH₂Cl₂:MeOH=10:1). ¹H-NMR (pyridine-d₅): 8.43 (d, 1H, J=8.5 Hz), 5.56 (d, 1H, J=3.7 Hz), 5.25 (m, 1H), 4.7-4.6 (m, 2H), 4.54 (d, 1H, J=3.0 Hz), 4.50 (t, 1H, J=6.0 Hz), 4.45-4.3 (m, 4H), 4.3-4.2 (m, 2H), 2.42 (t, 2H, J=7.4 Hz), 2.3-2.15 (m, 1H), 1.9-1.75 (m, 4H), 1.7-1.55 (m, 1H), 1.4-1.15 (m, 56H), 0.85 (t, 3H, J=6.7 Hz), 0.78 (t, 3H, J=7.1 Hz). MS (FAB) m/z: 747 (M+H+).

EXAMPLE 7

Synthesis of (2S,3S,4R)-1-O-(α-D-galactosyl)-2-(N-hexacosanoyl amino)-1,3,4-nonane triol (Compound 29)

The title compound was obtained using compound 7 and cerotinic acid by the same procedure for the synthesis of compounds 8, 14, 17, 20 and 23.
TLC: Rf=0.20 (CH₂Cl₂:MeOH=6:1). ¹H-NMR (pyridine-d₅): 8.44 (d, 1H, J=8.4 Hz), 5.56 (d, 1H, J=3.7 Hz), 5.50-5.19 (m, 1H), 4.69-4.61 (m, 2H), 4.54 (d, 1H, J=3.1 Hz), 4.52-4.47 (m, 1H), 4.45-4.34 (m, 4H), 4.31-4.23 (m, 2H), 2.43 (t, 2H, J=7.4 Hz), 2.28-2.17 (m, 1H), 1.92-1.73 (m, 4H), 1.70-1.53

(m, 1H), 1.38-1.15 (m, 54H), 0.85 (t, 3H, J=6.7 Hz), 0.73 (t, 3H, J=7.0 Hz). MS (FAB) m/z: 732 (M+).

EXAMPLE 8

Synthesis of (2S,3S,4R)-1-O-(α-D-galactosyl)-2-(N-pentacosanoyl amino)-1,3,4-nonane triol (Compound 30)

The title compound was obtained using compound 7 and pentacosanoic acid by the same procedure for the synthesis of compounds 8, 14, 17, 20 and 23.
TLC: Rf=0.53 (CH$_2$Cl$_2$:MeOH=6:1). $^1$H-NMR (CDCl$_3$:CD$_3$D=3:1): 4.92 (d, 1H, J=3.3 Hz), 4.20-4.15 (m, 1H), 3.96-3.93 (m, 1H), 3.92-3.85 (m, 1H), 3.82-3.65 (m, 6H), 3.60-3.52 (m, 2H), 2.21 (t, 2H, J=7.6 Hz), 1.62-1.26 (m, 52H), 0.90-0.85 (m, 6H). MS (FAB) m/z: 719 (M+H$^+$).

EXAMPLE 9

Synthesis of (2S,3S,4R)-1-O-(α-D-galactosyl)-2-(N-tricosanoyl amino)-1,3,4-nonane triol (Compound 31)

The title compound was obtained using compound 7 and tricosanoic acid by the same procedure for the synthesis of compounds 8, 14, 17, 20 and 23.
TLC: Rf=0.51 (CHCl$_3$:MeOH=4:1). $^1$H-NMR (CDCl$_3$:CD$_3$OD=3:1): 4.91 (d, 1H, J=3.1 Hz), 4.23-4.15 (m, 1H), 3.95-3.85 (m, 2H), 3.81-3.63 (m, 6H), 3.59-3.51 (m, 2H), 2.21 (t, 2H, J=7.5 Hz), 1.61-1.25 (m, 48H), 0.90-0.85 (m, 6H). MS (FAB) m/z: 690 (M+).

EXAMPLE 10

Synthesis of (2S,3S,4R)-1-O-(α-D-galactosyl)-2-(N-docosacosanoyl amino)-1,3,4-nonane triol (Compound 32)

The title compound was obtained using compound 7 and docosanoic acid by the same procedure for the synthesis of compounds 8, 14, 17, 20 and 23.
TLC: Rf=0.47 (CH$_2$Cl$_2$:MeOH=5:1). $^1$H-NMR (CDCl$_3$:CD$_3$OD=3:1): 4.90 (d, 1H, J=3.0 Hz), 4.27-4.20 (m, 1H), 3.96-3.92 (m, 1H), 3.91 (dd, 1H, J=10.5 Hz and 4.0 Hz), 3.82-3.65 (m, 6H), 3.58-3.51 (m, 2H), 2.22 (t, 2H, J=7.6 Hz), 1.70-1.21 (m, 46H), 0.90-0.85 (m, 6H), MS (FAB) m/z: 676 (M+).

EXAMPLE 11

Synthesis of (2S,3S,4R)-1-O-(α-D-galactosyl)-2-(N-heneicosanoyl amino)-1,3,4-nonane triol (Compound 33)

The title compound was obtained using compound 7 and heneicosanoic acid by the same procedure for the synthesis of compounds 8, 14, 17, 20 and 23.
TLC: Rf=0.33 (CH$_2$Cl$_2$:MeOH=6:1). $^1$H-NMR (CDCl$_3$:CD$_3$OD=3:1): 8.05 (d, 1H, J=7.9 Hz), 4.92 (d, 1H, J=3.3 Hz), 4.22 (m, 1H), 3.96 (m, 1H), 3.90 (dd, 1H, J=10.5 Hz and 4.1 Hz), 3.81-3.69 (m, 6H), 3.55 (m, 2H), 2.22 (t, 2H, J=7.6 Hz), 1.68-1.62 (m, 4H), 1.31-1.27 (m, 40H), 0.90-0.87 (m, 6H). MS (FAB) m/z: 662 (M+H$^+$).

EXAMPLE 12

Synthesis of (2S,3S,4R)-1-O-(α-D-galactosyl)-2-(N-eicosanoyl amino)-1,3,4-nonane triol (Compound 34)

The title compound was obtained using compound 7 and arachidonic acid by the same procedure for the synthesis of compounds 8, 14, 17, 20 and 23.
TLC: Rf=0.33 (CH$_2$Cl$_2$:MeOH=6:1). $^1$H-NMR (CDCl$_3$:CD$_3$OD=3:1): 4.86 (d, 1H, J=3.4 Hz), 4.16 (m, 1H), 3.90 (m, 1H), 3.85 (dd, 1H, J=10.5 Hz and 4.6 Hz), 3.74-3.61 (m, 6H), 3.50 (m, 2H), 2.17 (t, 2H, J=7.9 Hz), 1.62-1.56 (m, 4H), 1.25-1.21 (m, 38H), 0.85-0.81 (m, 6H). MS (FAB) m/z: 648 (M+H$^+$).

In addition, alpha-galactosylceramide (α-GC), NH and 3,4D were synthesized according to the methods of synthesis described in examples, and they were used as reference substances for the comparison of biological activity evaluation. Here, α-GC refers to (2S,3S,4R)-1-O-(α-D-galactosyl)-2-(N-hexacosanoyl amino)-1,3,4-octadecane triol, NH refers to (2S,3S,4R)-1-O-(2-amino-2-deoxy-α-D-galactosyl)-2-(N-hexacosanoyl amino)-1,3,4-octadecane triol and 3,4D refers to (2S)-1-O-(α-D-galactosyl)-2-(N-tetracosanoyl amino)-1-octadecanol. The structural formulae and spectral data of these compounds are shown below.

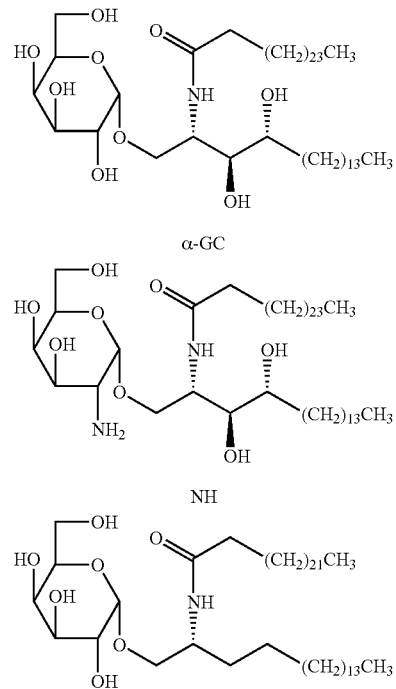

α-GC

NH 3,4D

COMPARATIVE EXAMPLE 1

(2S,3S,4R)-1-O-(2-deoxy-2-amino-2-deoxy-α-D-galactosyl)-2-(N-hexacosanoyl amino)-1,3,4-octadecane triol (Compound 35: NH)

TLC:Rf=0.67 (t-BuOH:CH$_3$OH:H$_2$O=4:1:1). $^1$H-NMR (CDCl$_3$:CD$_3$OD:D$_2$O=3:1:0.1): 5.10 (d, 1H, J=3.5 Hz), 3.47-3.94 (m, 11H), 2.24 (t, 2H, J=7.3 Hz), 1.26-1.54 (m, 72H), 0.88 (m, 6H). MS (ESI) m/z: 857.7 (M+H$^+$).

COMPARATIVE EXAMPLE 2

(2S,3S,4R)-1-O-(α-D-galactosyl)-2-(N-hexacosanoyl amino)-1,3,4-octadecane triol (Compound 36: α-GC)

TLC:Rf=0.75 (CHCl$_3$:MeOH=3:1). $^1$H-NMR (CDCl$_3$:CD$_3$OD=3:1): 4.90 (d, 1H, J=3.6 Hz), 3.56-3.90 (m, 11H), 2.21 (t, 2H, J=7.4 Hz), 1.27-1.61 (m, 72H), 0.89 (m, 6H). MS (ESI) m/z: 880.7 (M+H$^+$).

COMPARATIVE EXAMPLE 3

(2S)-1-O-(α-D-galactosyl)-2-(N-tetracosanoyl amino)-1,3,4-octadecanol (Compound 37: 3,4D)

TLC:Rf=0.48 (CHCl$_3$:MeOH=7:1). $^1$H-NMR (CDCl$_3$:CD$_3$OD=3:1): 4.90 (d, 1H, J=3.3 Hz), 3.42-3.95 (m, 9H), 2.19 (t, 2H, J=7.6 Hz), 1.27-1.62 (m, 72H), 0.89 (m, 6H). MS (MALDI) m/z: 820.74 (M+Na$^+$).

Biological Activity Evaluation

The biological activities of the compounds synthesized as described above were evaluated using the methods described below.

First, synthesized glycolipids [Compound 25 and α-GC (Compound 36)] were used, and an inhibition study for experimental autoimmune encephalomyelitis (EAE) was conducted.

Female C57BL6J(B6) mice, six to eight weeks in age, were immunized at the base of the tail using an emulsion of 100 μg of a peptide (Sequence No. 1) corresponding to 35-55 amino acid residue of myelin oligodendrocyte glycoprotein (MOG) in combination with killed Mycobacterium tuberculosis (H$_{37}$Ra). 200 ng of pertussis toxin was administered via a tail vein on the same day and 200 ng of pertussis toxin was administered intra-peritoneally 48 hours after inoculation for inducing EAE. Clinical observations and pathological study were conducted. Synthesized glycolipids were administered orally (400 ng/kg). DMSO (dimethyl sulfoxide) alone was administered to the control group.

The results are shown in Table 1. The clinical and pathological scores described below were used in the evaluations.

Clinical scores: 0: normal, 1: decline in tail tonicity, 2: limp tail and unstable gait, 3: mild hind limb weakness, 4: complete hind limb weakness, 5: fore and hind limb paralysis, 6: death.

Pathological scores: 0: normal, 1: leptomeningeal and adjacent subpial cell infiltration, 2: mild perivascular cuffing, 3: extensive perivascular cuffing, 4: cerebral parenchymal cell infiltration.

TABLE 1

| | Max. score | Onset | Incidence | Total score | Path. score |
|---|---|---|---|---|---|
| A) B6 mice, 0 day oral administration | | | | | |
| DMSO | 2.75 ± 0.38 | 12.00 ± 0.91 | 12/12 | 25.19 ± 4.03 | 1.92 ± 0.24 |
| α-GC | 2.41 ± 0.37 | 14.27 ± 0.98 | 12/12 | 20.32 ± 4.07 | 1.79 ± 0.38 |
| Compound 25 | 1.42 ± 0.33 | 14.80 ± 1.22 | 10/12 | 10.71 ± 3.23 | 1.00 ± 0.13 |
| B) B6 mice, 8$^{th}$ day oral administration | | | | | |
| DMSO | 3.30 ± 0.26 | 12.60 ± 1.83 | 7/7 | 22.70 ± 3.12 | |
| α-GC | 3.00 ± 0.29 | 13.86 ± 0.99 | 7/7 | 17.50 ± 2.74 | |
| Compound 25 | 2.25 ± 0.51 | 16.43 ± 1.95 | 6/7 | 10.94 ± 3.40 | |
| C) NKT knockout mice, 0 day oral administration | | | | | |
| DMSO | 4.00 ± 0.11 | 11.29 ± 0.97 | 6/6 | 35.79 ± 4.73 | |
| α-GC | 3.67 ± 0.42 | 13.33 ± 1.41 | 6/6 | 32.25 ± 6.66 | |
| Compound 25 | 3.64 ± 0.28 | 12.43 ± 0.53 | 6/6 | 34.36 ± 4.15 | |

An EAE suppression effect was observed in the group treated with Compound 25, but no suppression effect was observed in α-GC treated group. The suppression effect was observed in the Compound 25 treated group even in the pathological test. Since the EAE suppression effect due to Compound 25 could not be observed in NKT knockout mice (TCR J alpha 281 knockout mice), NKT cells were thought to be involved in the effect.

Figure 3:
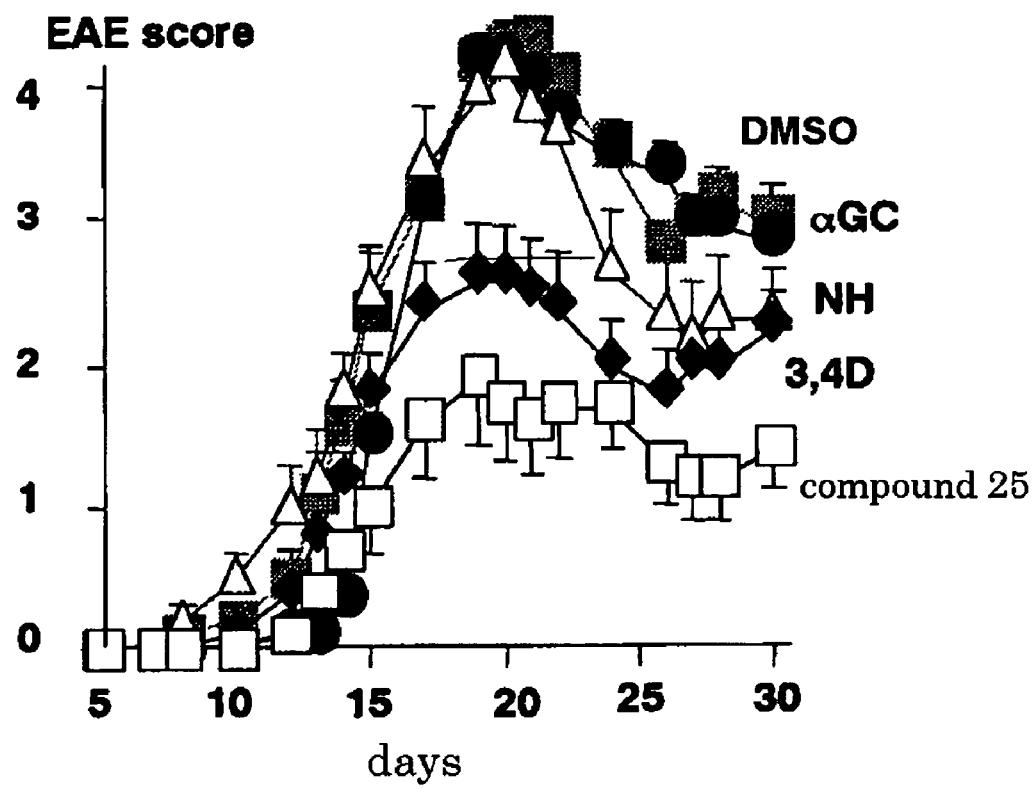
FIG. 3 is a graph indicating the results of an experimental autoimmune encephalomyelitis (EAE) suppression study involving dimethyl sulfoxide (DMSO), (2S, 3S, 4R)-1-O-(2-deoxy-2-amino-2-deoxy-α-D-galactosyl)-2-(N-hexacosanoyl amino)-1,3,4 octadecane triol (NH), (2S, 3S, 4R)-1-O-(α-D-galactosyl)-2-(N-hexacosanoyl amino)-1,3,4 octadecane triol (α-GC), (2S)-1-O-(α-D-galactosyl)-2-(N-hexacosanoyl amino)-1,3,4 octadecanol (3,4D) and (2S, 3S, 4R)-1-O-(α-D-galactosyl)-2-(N-hexacosanoyl amino)-1,3,4 nonane triol (Compound 25).

Next, EAE was induced using the method described in the aforementioned autoimmune encephalomyelitis (EAE) suppression test, and the EAE suppression effect of intraperitoneal administration of Compound 25 (100 μg/kg) was studied. The results are shown in FIG. 3. The result shows that intraperitoneal administration has similar EAE suppression effects to oral treatments.

Next, synthesized glycolipids (Compound 25 and α-GC) and DMSO were used to study the mechanism of experimental autoimmune encephalomyelitis (EAE) suppression.

EAE was induced using the method described above, and the role of IL-4 in the EAE suppression effect associated with Compound 25 administration was investigated. Anti-IL-4 antibody (1 mg/ml) was simultaneous administered intraperitoneally. The results are shown in Table 2.

TABLE 2

| | Max. score | Onset | Incidence | Total score |
|---|---|---|---|---|
| anti-IL-4 (−) | | | | |
| DMSO | 3.78 ± 0.24 | 9.67 ± 0.97 | 10/10 | 39.94 ± 3.65 |
| α-GC | 4.00 ± 0.25 | 9.10 ± 0.84 | 10/10 | 45.00 ± 3.87 |
| Compound 25 | 2.75 ± 0.37 | 11.00 ± 0.78 | 9/10 | 26.05 ± 4.16 |
| anti-IL-4 (+) | | | | |
| DMSO | 4.00 ± 0.29 | 8.57 ± 0.84 | 10/10 | 42.50 ± 3.40 |
| α-GC | 3.79 ± 0.29 | 11.29 ± 1.58 | 10/10 | 37.00 ± 5.02 |
| Compound 25 | 3.50 ± 0.15 | 9.43 ± 0.90 | 10/10 | 38.79 ± 2.94 |

The EAE suppression effect achieved by Compound 25 administration disappeared when anti-IL-4 antibody was administered indicating that IL-4 was important in EAE suppression.

Figure 4:
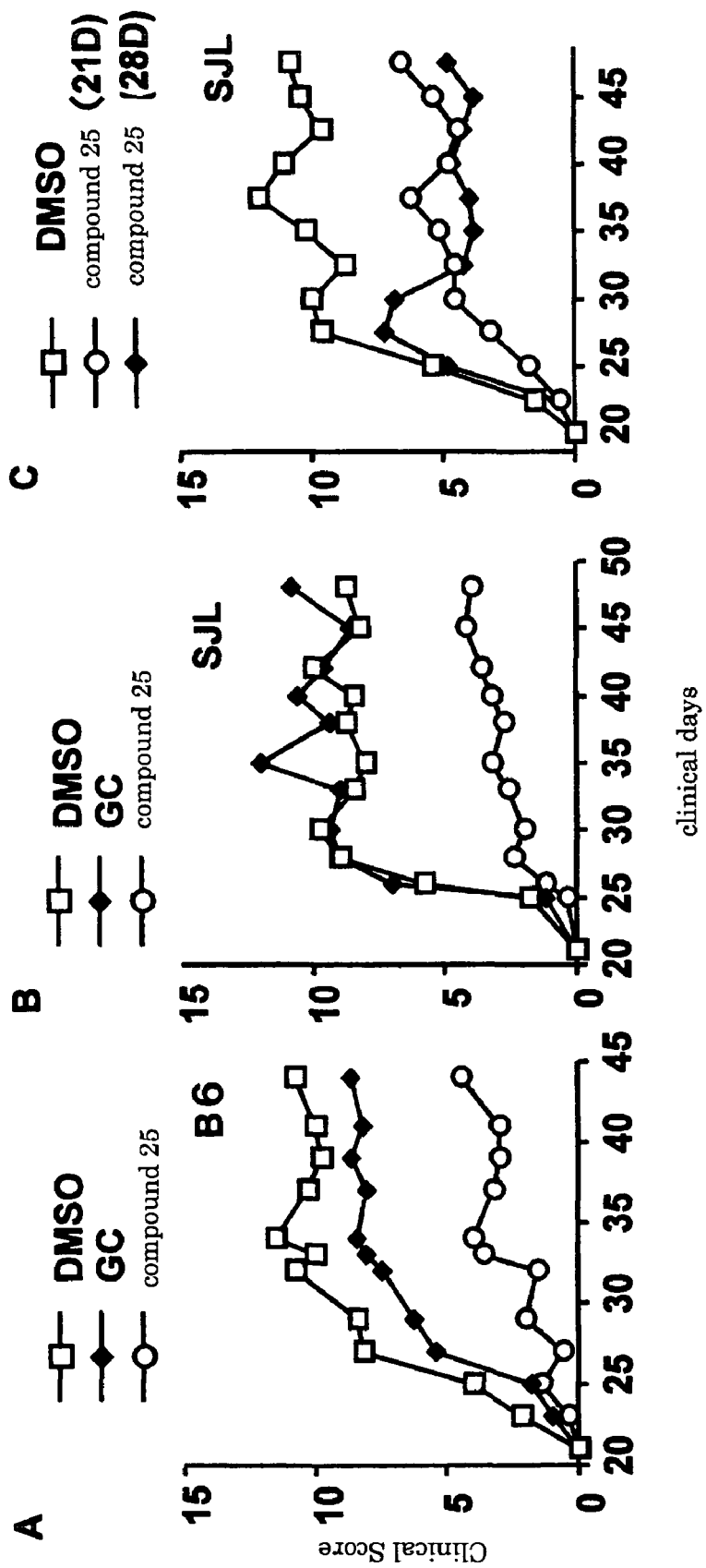
FIG. 4 is a graph indicating the results of a collagen induced arthrisis (CIA) suppression study involving dimethyl sulfoxide (DMSO), (2S, 3S, 4R)-1-O-(α-D-galactosyl)-2-(N-hexacosanoyl amino)-1,3,4 octadecane triol (GC) and (2S, 3S, 4R)-1-O-(α-D-galactosyl)-2-(N-hexacosanoyl amino)-1,3,4 nonane triol (Compound 25).

Next, a collagen arthritis (CIA) suppression test was conducted. The results are shown in FIG. 4.

A) Male mice C57BL6 six to eight weeks in age were immunized at the base of the tail using an emulsion of 100 μg of a tri Type II collagen in combination with killed Mycobacterium tuberculosis (H$_{37}$Ra). On the 21st day, the mice were additionally immunized using the same emulsion and clinical signs were observed. The synthesized glycolipids (500 μg/kg) were administered intraperitoneally twice a week from the time of the additional immunization. The control group received DMSO only.

Clinical score:0: No sign, 1: Swelling and redness observed in one small joint such as a finger joint, 2: Swelling and redness observed in at least two small joints or relatively large joint such as wrists and ankles, 3: Swelling and redness observed in one entire hand or foot, 4: Maximum swelling in one entire hand or foot. The score represents a total for both hands and feet. A suppression effect was observed upon Compound 25 administration in B6 mice with collagen induced arthritis.

B) Male SJL mice six to eight weeks in age were immunized at the base of the tail using an emulsion of 200 µg of a bovine Type II collagen in combination with killed Mycobacterium tuberculosis ($H_{37}Ra$). On the 21st day, the mice were additionally immunized using the same emulsion and clinical signs were observed. The synthesized glycolipids (500 µg/kg) were administered intraperitoneally twice a week from the time of the additional immunization. The control group received DMSO only. The collagen induced arthritis in SJL mice was effectively suppressed upon Compound 25 administration.

C) Male SJL mice six to eight weeks in age were immunized at the base of the tail using an emulsion of 200 µg of a bovine Type II collagen in combination with killed Mycobacterium tuberculosis ($H_{37}Ra$). On the 21st day, the mice were additionally immunized using the same emulsion and clinical signs were observed. The synthesized glycolipids (500 µg/kg) were administered intraperitoneally twice a week from the time of the additional immunization or 28 days from the appearance of symptoms. The control group received DMSO only. Collagen induced arthritis was effectively suppressed upon Compound 25 administration upon appearance of symptoms.

Figure 5:
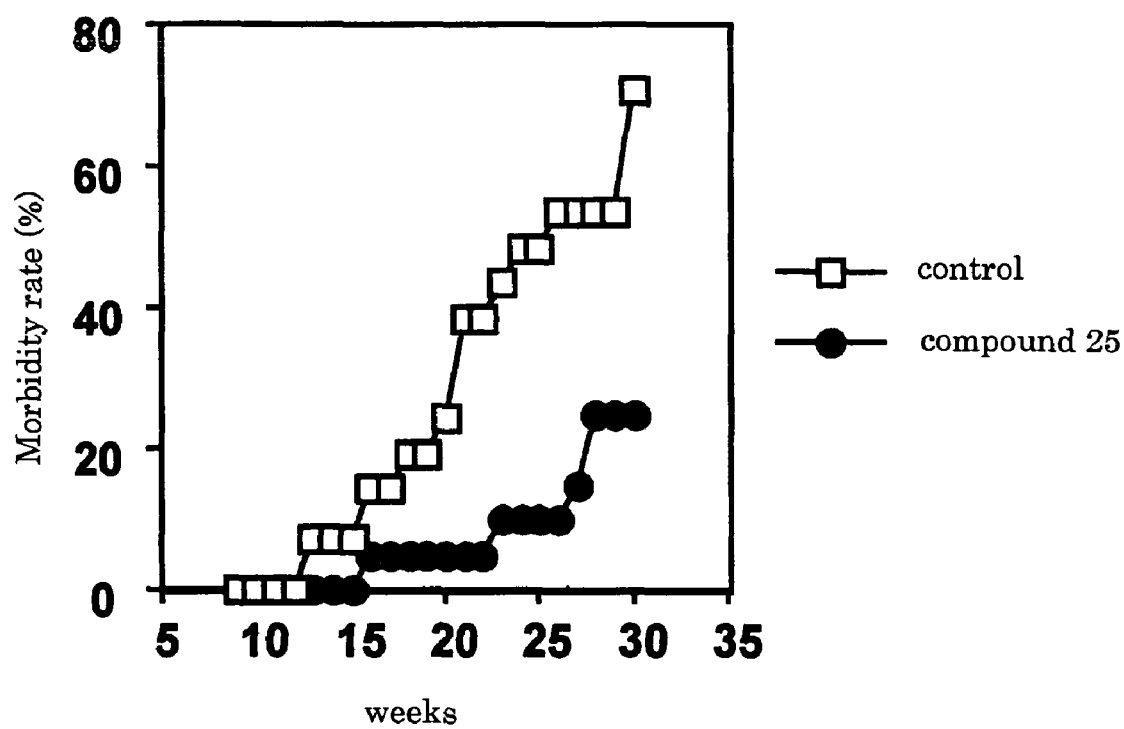
FIG. 5 indicates the results of a diabetes onset suppression test in NOD mice, involving a control group and a group treated with (2S, 3S, 4R)-1-O-(α-D-galactosyl)-2-(N-hexacosanoyl amino)-1,3,4 nonane triol (Compound 25).

Next, a suppression test of diabetes incidence was conducted using NOD mice. The results are shown in FIG. 5. The diabetes incidence was observed significantly suppressed by intraperitoneal administration of compound 25 (100 µg/kg) twice to NOD mice four weeks in age.

Figure 6:
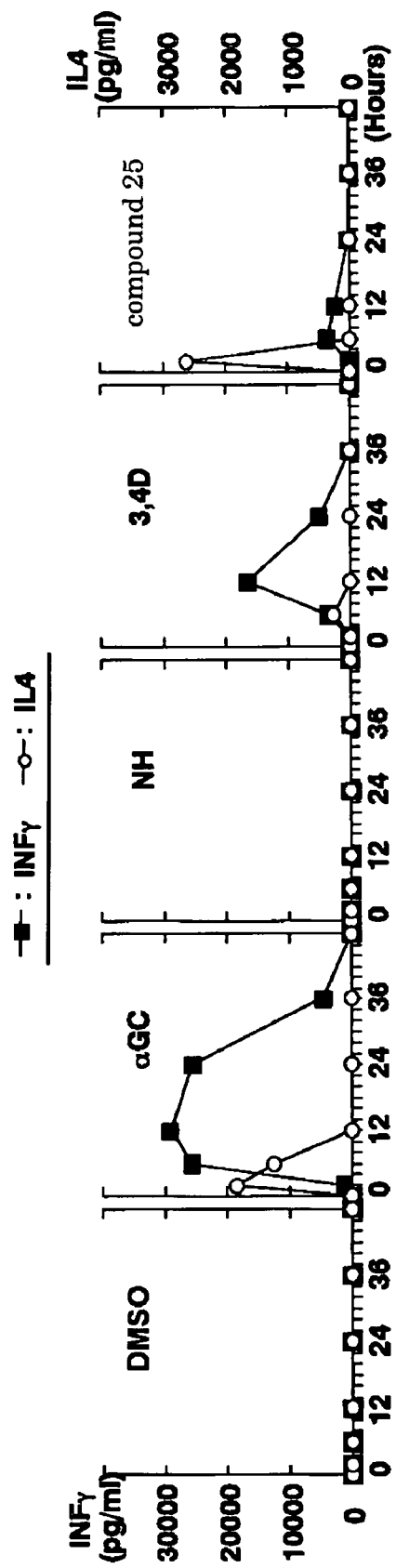
FIG. 6 is a graph indicating the results of serum cytokine measurements involving dimethyl sulfoxide (DMSO), (2S, 3S, 4R)-1-O-(2-deoxy-2-amino-2-deoxy-α-D-galactosyl)-2-(N-hexacosanoyl amino)-1,3,4 octadecane triol (NH), (2S, 3S, 4R)-1-O-(α-D-galactosyl)-2-(N-hexacosanoyl amino)-1,3,4 octadecane triol (α-GC), (2S)-1-O-(α-D-galactosyl)-2-(N-hexacosanoyl amino)-1,3,4 octadecanol (3,4D) and (2S, 3S, 4R)-1-O-(α-D-galactosyl)-2-(N-hexacosanoyl amino)-1,3,4 nonane triol (Compound 25), in which serum levels of INF-γ and IL-4 cytokines are measured.

Next, cytokines in blood were measured and the results are shown in FIG. 6. A large amount of cytokine is known to be released into the blood in a short duration of time when NKT cells are stimulated. Therefore, serum INF-γ and IL-4 levels with elapsed time were measured using the ELISA method when the synthesized glycolipids were administered to mice. As reported previously, INF-γ was predominantly formed upon α-GC administration, but IL-4 was predominantly formed upon Compound 25 administration.

Figure 7:
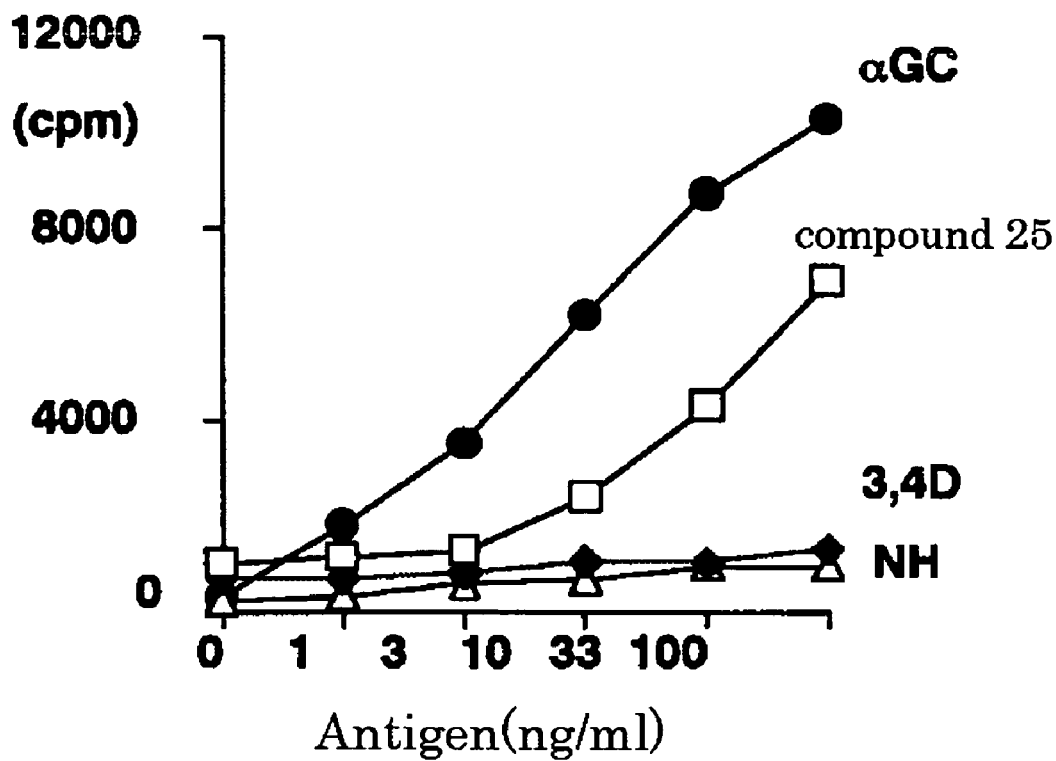
FIG. 7 is a graph indicating the results of proliferative response assays for spleen cells involving (2S, 3S, 4R)-1-O-(2-deoxy-2-amino-2-deoxy-α-D-galactosyl)-2-(N-hexacosanoyl amino)-1,3,4 octadecane triol (NH), (2S, 3S, 4R)-1-O-(α-D-galactosyl)-2-(N-hexacosanoyl amino)-1,3,4 octadecane triol (α-GC), (2S)-1-O-(α-D-galactosyl)-2-(N-hexacosanoyl amino)-1,3,4 octadecanol (3,4D) and (2S, 3S, 4R)-1-O-(α-D-galactosyl)-2-(N-hexacosanoyl amino)-1,3,4 nonane triol (Compound 25).

Next, spleen cell proliferation reactions were measured, and the results are shown in FIG. 7. Murine spleen cells were isolated, and the proliferation reaction for the synthesized glycolipids were measured using thymidine incorporation into the cells as the indicator. The spleen cells exhibited significant proliferation reaction toward Compound 25.

Figure 8:
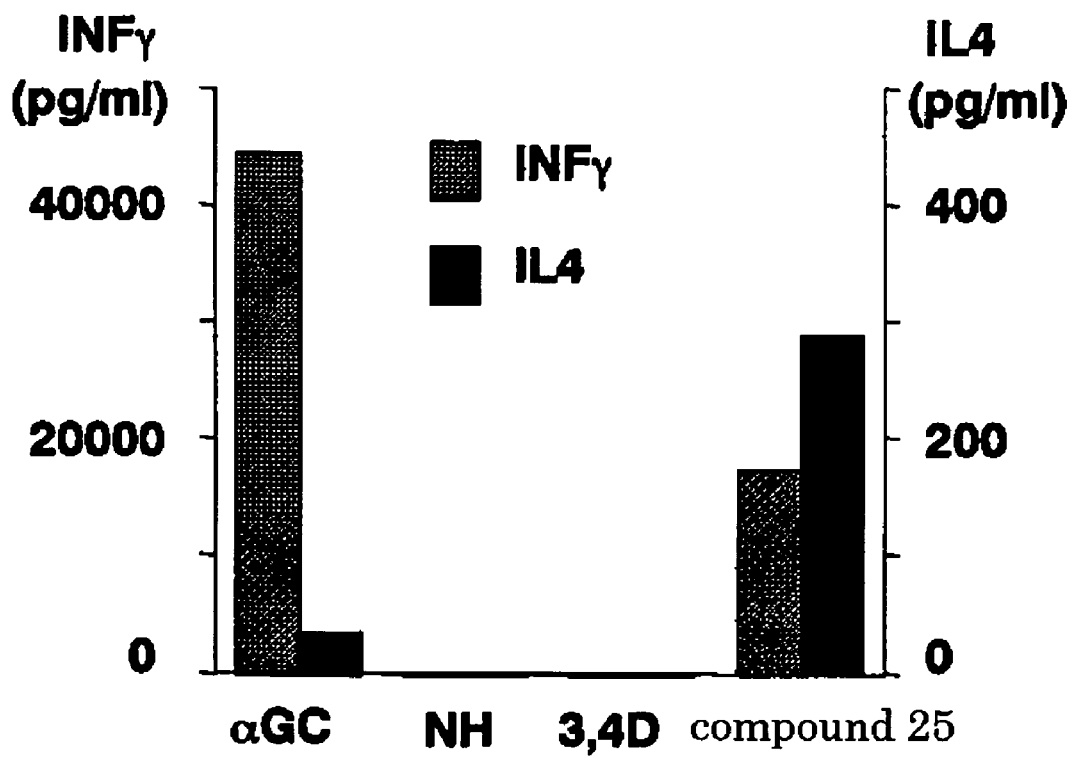
FIG. 8 is a graph indicating the results of spleen cell cytokine production assays involving (2S, 3S, 4R)-1-O-(2-deoxy-2-amino-2-deoxy-α-D-galactosyl)-2-(N-hexacosanoyl amino)-1,3,4 octadecane triol (NH), (2S, 3S, 4R)-1-O-(α-D-galactosyl)-2-(N-hexacosanoyl amino)-1,3,4 octadecane triol (α-GC), (2S)-1-O-(α-D-galactosyl)-2-(N-hexacosanoyl amino)-1,3,4 octadecanol (3,4D) and (2S, 3S, 4R)-1-O-(α-D-galactosyl)-2-(N-hexacosanoyl amino)-1,3,4 nonane triol (Compound 25), in which levels of INF-γ and IL-4 cytokines are measured.

Next, spleen cell cytokine measurements were conducted, and the results are shown in FIG. 8. Murine spleen cells were isolated, and levels of INF-γ and IL-4 formation due to synthesized glycolipids were measured using the ELISA method. INF-γ was predominantly formed upon α-GC administration but IL-4 was predominantly formed upon Compound 25 administration as observed in treating mice.

Figure 9:
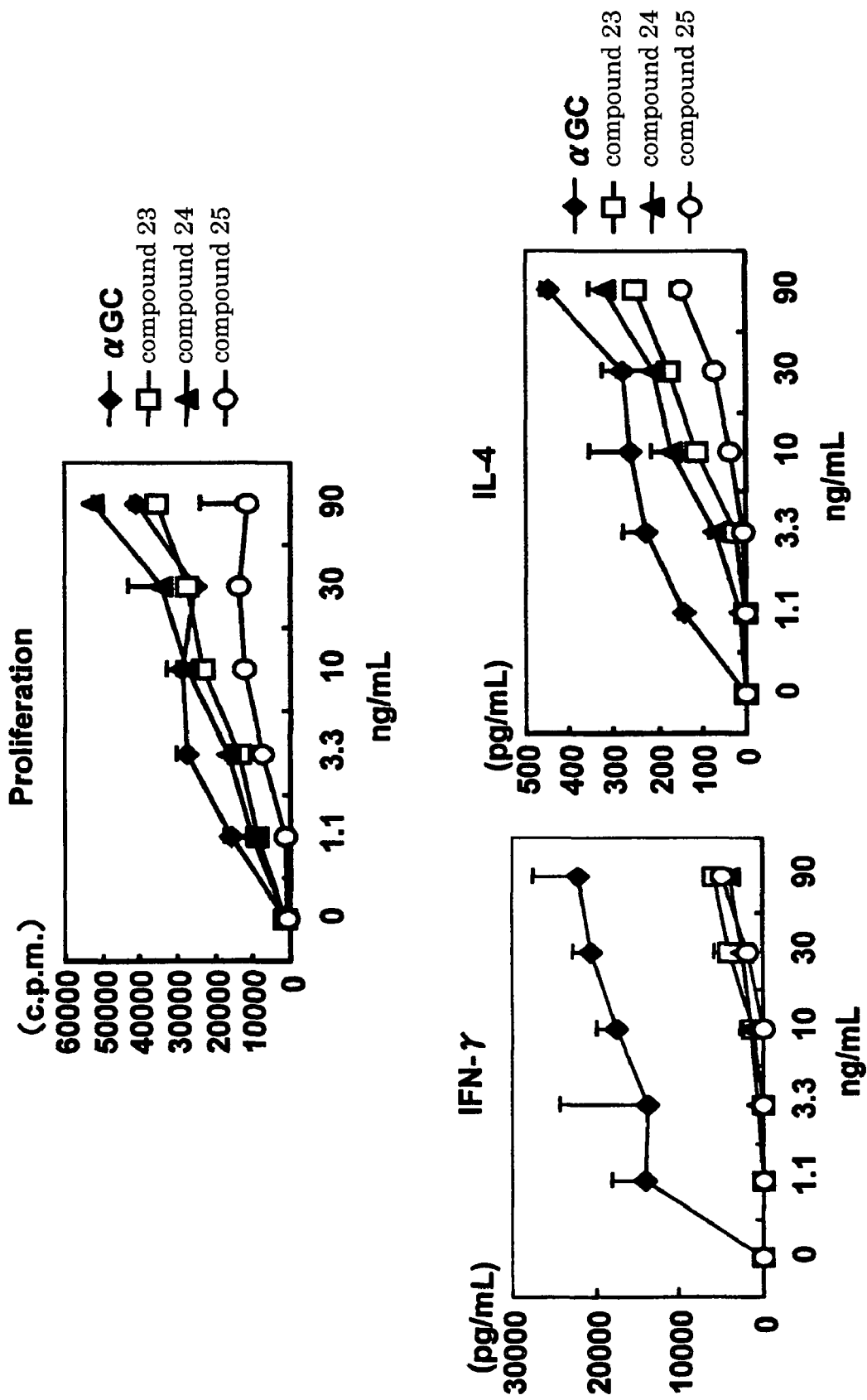
FIG. 9 indicates the results of spleen cell proliferative response assays and INF-γ and IL-4 cytokine measurements involving (2S, 3S, 4R)-1-O-(α-D-galactosyl)-2-(tetracosanoyl amino)-1,3,4 octane triol (Compound 23), (2S, 3S, 4R)-1-O-(α-D-galactosyl)-2-(N-hexacosanoyl amino)-1,3,4 heptane triol (Compound 24) (2S, 3S, 4R)-1-O-(α-D-galactosyl)-2-(N-hexacosanoyl amino)-1,3,4 nonane triol (Compound 25).

Next, spleen cell proliferation reactions and cytokine measurements were conducted, and the results are shown in FIG. 9. Murine spleen cells were isolated, and the proliferation reactions for synthesized glycolipids were measured using thymidine incorporation into the cells as the indicator. Significant spleen cell proliferation reaction was exhibited with Compounds 23, 24 and 25. Murine spleen cells were isolated, and levels of INF-γ and IL-4 formation due to the synthesized glycolipids were measured using the ELISA method. INF-γ was predominantly formed upon α-GC administration but IL-4 was predominantly formed upon Compound 23, 24 and 25 administration.

Figure 10:
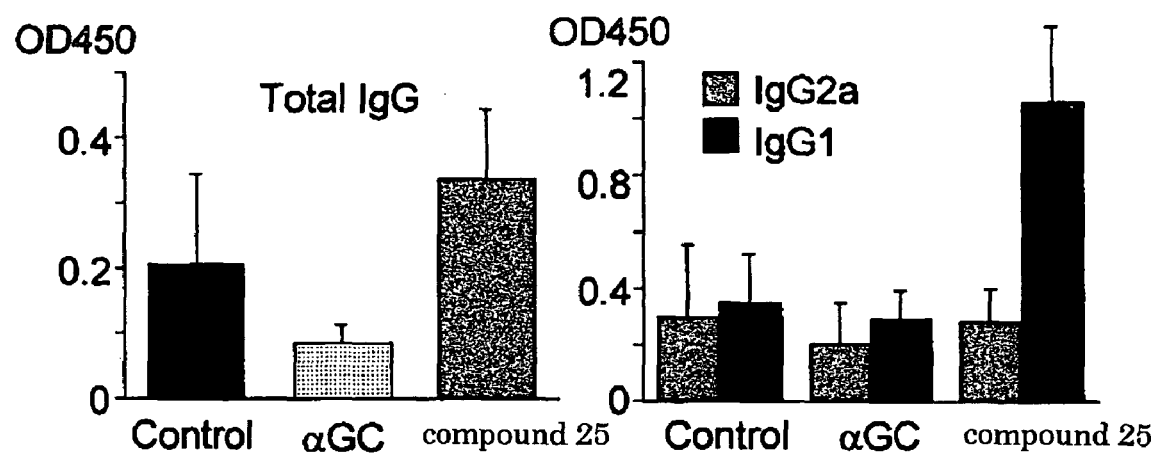
FIG. 10 is a graph indicating the results of serum anti-MOG antibody measurements involving a control, (2S, 3S, 4R)-1-O-(α-D-galactosyl)-2-(N-hexacosanoyl amino)-1,3,4 octadecane triol (α-GC), and (2S, 3S, 4R)-1-O-(α-D-galactosyl)-2-(N-hexacosanoyl amino)-1,3,4 nonane triol (Compound 25). The right axis of the graph represents IgG1 antibody measurements and the left axis represents IgG2a antibody measurements.

Next, serum anti-MOG antibody measurements were conducted, and the results are shown in FIG. 10. The ELISA method was used to measure levels of anti-MOG antibody and its isotype in the group treated using synthesized glycolipids. The anti-MOG antibody level rose in the group treated using Compound 25. As far as the isotype was concerned, the IgG1 level rose significantly indicating that the reaction to MOG was biased toward Th2.

---

What is claimed is:

1. A glycolipid represented by the formula below (I),

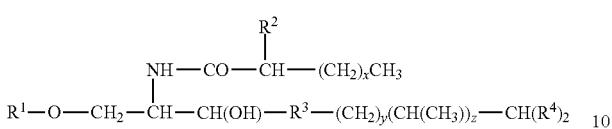

wherein, $R^1$ is an aldopyranose group, $R^2$ is a hydrogen atom or a hydroxyl group, $R^3$ is $CH_2$—, —CH(OH)—$CH_2$— or —CH=CH—, $R^4$ is a hydrogen atom, x is 0-35, y and z represent integers satisfying y+z=0-3.

2. The glycolipid as in claim 1 wherein $R^1$ is α-D-galactopyranosyl.

3. The glycolipid as in claim 2 wherein $R^3$ is —$CH_2$— or —CH(OH)—$CH_2$— and x is 10-32.

4. The glycolipid as in claim 3 wherein $R^3$ is —CH(OH)—$CH_2$—.

5. The glycolipid as in claim 3 wherein $R^2$ is a hydrogen atom, x is 11-23 and z is 0.

6. The glycolipid as in claim 1 wherein $R^2$ is a hydrogen atom, x is 11-23 and z is 0.

7. The glycolipid as in claim 1, which is selected from the group consisting of (2S,3S,4R)-1-O(α-D-galactosyl)-2-(N-tetracosanoyl amino)-1,3,4-octane triol, (2S,3S,4R)-1-O(α-D-galactosyl)-2-(N-tetracosanoyl amino)-1,3,4-heptane triol, and (2S,3S,4R)-1-O(α-D-galactosyl)-2-(N-tetracosanoyl amino)-1,3,4-nonane triol.

8. The glycolipid as in claim 7, which is

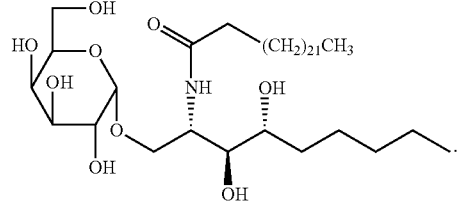

9. A pharmaceutical composition comprising as the active ingredient the glycolipid as in claim 1.

10. A pharmaceutical composition comprising as the active ingredient the glycolipid as in claim 2.

11. A pharmaceutical composition comprising as the active ingredient the glycolipid as in claim 5.

12. A pharmaceutical composition comprising as the active ingredient the glycolipid as in claim 6.

13. A pharmaceutical composition comprising as the active ingredient the glycolipid as in claim 7.

14. A pharmaceutical composition comprising as the active ingredient the glycolipid as in claim 8.

* * * * *

SEQUENCE LISTING

<160> NUMBER OF SEQ ID NOS: 1

<210> SEQ ID NO 1
<211> LENGTH: 21
<212> TYPE: PRT
<213> ORGANISM: Artificial
<220> FEATURE:
<223> OTHER INFORMATION: Residue of myelin oligodendrocyte glycoprotein
<220> FEATURE:
<221> NAME/KEY: PEPTIDE
<222> LOCATION: (1)..(21)

<400> SEQUENCE: 1

Met Glu Val Gly Trp Tyr Arg Ser Pro Phe Ser Arg Val Val His Leu
1               5                   10                  15

Tyr Arg Asn Gly Lys
            20